United States Patent
Kacmar et al.

(10) Patent No.: US 10,767,204 B2
(45) Date of Patent: Sep. 8, 2020

(54) ADVANCED AUGER AND FILTRATION SYSTEM FOR THE SACCHARIFICATION OF BIOMASS

(71) Applicant: Edeniq, Inc., Visalia, CA (US)

(72) Inventors: James Kacmar, Visalia, CA (US); Rich Kleinke, Visalia, CA (US); Bernard Cooker, Visalia, CA (US); Chris Kalinowski, Visalia, CA (US); Jon Van Volkinburg, Clovis, CA (US)

(73) Assignee: Edeniq, Inc., Visalia, CA (US)

( * ) Notice: Subject to any disclaimer, the term of this patent is extended or adjusted under 35 U.S.C. 154(b) by 483 days.

(21) Appl. No.: 14/654,411

(22) PCT Filed: Dec. 20, 2013

(86) PCT No.: PCT/US2013/077133
§ 371 (c)(1),
(2) Date: Dec. 28, 2015

(87) PCT Pub. No.: WO2014/100685
PCT Pub. Date: Jun. 26, 2014

(65) Prior Publication Data
US 2015/0344921 A1    Dec. 3, 2015

Related U.S. Application Data

(60) Provisional application No. 61/745,137, filed on Dec. 21, 2012.

(51) Int. Cl.
| | |
|---|---|
| *C12P 19/02* | (2006.01) |
| *C12P 7/10* | (2006.01) |
| *C12M 1/06* | (2006.01) |
| *C12M 1/00* | (2006.01) |
| *C13K 1/02* | (2006.01) |
| *C07H 1/08* | (2006.01) |
| *C12P 19/14* | (2006.01) |

(52) U.S. Cl.
CPC ............... *C12P 19/02* (2013.01); *C07H 1/08* (2013.01); *C12M 27/02* (2013.01); *C12M 27/20* (2013.01); *C12M 47/10* (2013.01); *C12P 7/10* (2013.01); *C12P 19/14* (2013.01); *C13K 1/02* (2013.01); *Y02E 50/16* (2013.01)

(58) Field of Classification Search
CPC .. C12P 19/02; C12P 7/10; C12P 19/14; C07H 1/08; C12M 27/02; C12M 27/20; C12M 47/10; C13K 1/02; Y02E 50/16
USPC .......................................................... 435/183
See application file for complete search history.

(56) References Cited

U.S. PATENT DOCUMENTS

| | | |
|---|---|---|
| 4,338,399 A | 7/1982 | Weil et al. |
| 4,556,430 A | 12/1985 | Converse et al. |
| 5,726,046 A | 3/1998 | Farone et al. |
| 5,782,982 A | 7/1998 | Farone et al. |
| 2009/0176286 A1 | 7/2009 | O'Connor et al. |

FOREIGN PATENT DOCUMENTS

EP    2336291 A1    6/2011

OTHER PUBLICATIONS

Xiao et al., Effects of Sugar Inhibition on Cellulases and β-Glucosidase During Enzymatic Hydrolysis of Softwood Substrates, Applied Biochemistry and Biotechnology, vol. 113-116, 2004, pp. 1115-1125.*
International Search Report and Written Opinion dated May 26, 2014 of International Patent Application No. PCT/US2013/077133, 14 pages.

* cited by examiner

*Primary Examiner* — Jennifer M. H. Tichy
(74) *Attorney, Agent, or Firm* — Kilpatrick Townsend & Stockton LLP

(57) ABSTRACT

The present disclosure provides methods and systems for generating sugars from biomass. The methods and systems provide increased yields of carbohydrates and fermentable sugars by combining enzyme recycling with removal of saccharification enzyme inhibitors and increased solids loading.

16 Claims, 22 Drawing Sheets

ADVANCED AUGER AND FILTRATION SYSTEM FOR THE SACCHARIFICATION OF BIOMASS

CROSS-REFERENCES TO RELATED APPLICATIONS

The present application is a National Stage of International Application No. PCT/US2013/077133, filed Dec. 20, 2013, and which claims benefit of priority to U.S. Provisional Patent Application No. 61/745,137, filed Dec. 21, 2012, which is incorporated by reference herein in its entirety.

BACKGROUND OF THE INVENTION

Biofuels such as ethanol can be produced from cellulosic biomass. While cellulosic ethanol production is currently possible, better efficiency in converting cellulosic biomass to biofuels will make the production of cellulosic biofuels more economically viable.

BRIEF SUMMARY OF THE INVENTION

The present invention provides methods and systems for treating lignocellulosic biomass to produce useful products such as carbohydrates and fermentable sugars. The methods and systems provide increased yields of carbohydrates and fermentable sugars by combining enzyme recycling with removal of saccharification enzyme inhibitors and increased solids loading. In one aspect, the invention provides a method for generating sugar from biomass. In one embodiment, the method comprises
  (a) contacting the biomass with enzymes under conditions suitable to hydrolyze components of the biomass to sugars, thereby producing a mixture of solids, liquids, and sugars;
  (b) separating the mixture into a liquid phase containing sugars and a solids phase;
  (c) incubating the solids phase under conditions suitable to hydrolyze components of the solid phase to sugars, thereby producing additional sugars;
  (d) separating the liquid phase into a permeate comprising dissolved solids and sugars and a retentate comprising undissolved solids, enzymes, and sugars; and
  (e) combining the washed retentate with the biomass or solids phase under conditions wherein the biomass is converted to sugars.

In some embodiments, the retentate is combined with additional untreated or unhydrolyzed biomass under conditions suitable to hydrolyze components of the biomass to sugars.

In some embodiments, the method further comprises washing the retentate to remove at least a portion of the sugars, thereby forming a washed retentate. The washed retentate is further separated into a liquid comprising sugars and solids comprising enzymes. In some embodiments, the washed retentate comprises less than 1.5%, 1%, or 0.5 w/v sugars. In some embodiments, the sugars are further concentrated by reverse osmosis.

In some embodiments, the liquid phase is separated from the solids phase by a screen, vibrating screen, a press, or a centrifuge. In some embodiments, the liquid phase is incubated under conditions suitable to produce sugars.

In some embodiments, the permeate is separated from the retentate by a filter or membrane.

In some embodiments, the method further comprises separating the permeate into a concentrated sugars portion and a liquid portion by reverse osmosis.

In some embodiments, the biomass comprises a slurry of at least about 5%, at least about 10%, at least about 15%, at least about 20%, at least about 25%, at least about 30%, or at least about 35% solids.

In some embodiments, the method further comprises washing the solids phase to remove at least a portion of the sugars, thereby forming a washed solids phase.

In some embodiments, the method further comprises separating the washed solids phase into a liquid comprising sugars, and solids.

In some embodiments, the contacting occurs in an auger. In some embodiments, the conditions suitable to hydrolyze components of the biomass to sugars comprise a counter-current flow such that the liquid phase moves in an opposite direction to the solid phase.

In some embodiments, the method further comprises concentrating the solids phase and separating at least a portion of any remaining liquid from the solids.

In some embodiments, the method is a batch process. In some embodiments, the method is a continuous process.

In another embodiment, the method comprises:
  (a) contacting the biomass with enzymes under conditions suitable to hydrolyze components of the biomass to sugars, thereby producing a mixture of solids, liquids, and sugars;
  (b) separating the mixture into a liquid phase and a solids phase;
  (c) combining the washed solids phase with the biomass under conditions wherein the biomass is converted to additional sugars.

In some embodiments, the method further comprises washing the solids phase to remove at least a portion of the sugars, thereby forming a washed solids phase. The washed solids phase can be further separated into a filtrate (i.e., a second liquid phase) and a retentate (i.e., a second solids phase), and the retentate is combined with the biomass and/or solids phase. In some embodiments, the filtrate/second liquid phase is separated into a permeate and a retentate, and the retentate is combined with the biomass and/or solids phase, and the permeate comprises sugars.

In some embodiments, the method further comprises separating the liquid phase into a permeate comprising dissolved solids and sugars and a retentate comprising undissolved solids, enzymes, and sugars;
  (a) washing the retentate to remove sugars, thereby forming a washed retentate; and
  (b) combining the washed retentate with the biomass or solids phase under conditions wherein the biomass is converted to sugars.

In some embodiments, the permeate is further separated into a concentrated sugars portion and a liquid portion.

In a third embodiment, the method comprises:
  (a) contacting the biomass with enzymes under conditions suitable to hydrolyze components of the biomass to sugars, thereby producing a mixture of solids, liquids, and sugars;
  wherein the conditions comprise a counter-current flow such that the liquids move in an opposite direction to the solids;
  (b) separating the mixture into a liquid phase and a solids phase;
  (c) incubating the solids phase under conditions suitable to hydrolyze components of the solid phase to sugars, thereby producing sugars;

(d) separating the liquid phase into a permeate comprising dissolved solids and sugars and a retentate comprising undissolved solids, enzymes, and sugars;

(e) combining the retentate with the biomass or solids phase under conditions wherein the biomass is converted to sugars.

In some embodiments, the method further comprises:

(a) washing the retentate to remove at least a portion of the sugars, thereby forming a washed retentate; and (b) combining the washed retentate with the biomass or solids phase under conditions wherein the biomass is converted to sugars.

In some embodiments, the method further comprises contacting the solids with additional biomass under conditions suitable to hydrolyze components of the biomass to sugars.

In some embodiments, the sugars are fermented under conditions suitable to produce ethanol.

In another aspect, the invention provides a system for treating biomass. In one embodiment, the system comprises: a first auger, the first auger comprising: a solids inlet, a screw inside the auger to direct a solid mass in the auger from a first end to a second end, a liquid outlet at the first end, and a solids outlet at the second end;

a separator suitable for separating the biomass into a liquid phase and a solids phase and positioned between (i) the liquid outlet and (ii) the screw and the solids outlet; and a second auger comprising: an inlet in fluid communication with the solids outlet for receiving a solids mass from the first auger; and a solids outlet.

In some embodiments, the system further comprises a second separator suitable for separating the biomass into a liquid phase and a solids phase and positioned between (i) the solids outlet of the first auger and (ii) the inlet of the second auger, wherein the second separator is in fluid communication with the solids outlet of the first auger and the inlet of the second auger.

In some embodiments, the first and/or second separator is a screen, a vibrating screen, or a press. In some embodiments, the first and/or second separator is in fluid communication with a filter suitable for separating the liquid phase into a filtrate and retentate. In some embodiments, the filter is in fluid communication with the liquid outlet of the first auger and the inlet of the first and/or second auger.

In some embodiments, the screw transports the solids mass in a direction opposite that of liquid flow inside the auger. In some embodiments, the auger is inclined such that the liquid outlet is lower than the solids outlet.

In some embodiments, the first and/or second auger further comprises additional inlets for adding biomass, solids, or enzymes.

In some embodiments, the system further comprises at least one additional auger comprising:

an inlet in fluid communication with the solids outlet of the first and/or second auger; and a solids outlet;

wherein the at least one additional auger is aligned in series with the first and second augers such that a solid mass is directed through the series.

In some embodiments, the solids outlet of at least one of the augers is in fluid communication with a third separator suitable for removing liquids from the treated biomass.

DEFINITIONS

Unless defined otherwise, all technical and scientific terms used herein have the same meaning as commonly understood by one of ordinary skill in the art to which this invention pertains. Although essentially any methods and materials similar to those described herein can be used in the practice or testing of the present invention, only exemplary methods and materials are described. For purposes of the present invention, the following terms are defined below.

The terms "a," "an," and "the" include plural referents, unless the context clearly indicates otherwise.

The term "dissolved solids" refers to sugars, soluble carbohydrates, polysaccharides, residual lignin, and other such substances that are not retained by solid-liquid separation methods. Exemplary solid-liquid separation methods include, but are not limited to, membrane filtration, tangential flow filtration (TFF), centrifugation, sedimentation and flotation.

The term "conditions suitable to hydrolyze components of the biomass to sugars" refers to contacting the solids phase biomass with hydrolytic enzymes including, but not limited to, cellulase, hemicellulase and auxiliary enzymes or proteins in order to produce fermentable sugars from polysaccharides in the biomass. The conditions can further include a pH that is optimal for the activity of saccharification enzymes, for example, a pH range of about 4.0 to 7.0. The conditions can further include a temperature that is optimal for the activity of saccharification enzymes, for example, a temperature range of about 35° C. to 75° C.

The term "permeate" refers to the liquid or fluid that passes through a porous membrane or filter. If a filter is used, the term is synonymous with "filtrate".

The term "retentate" refers to the material that does not pass through a porous membrane or filter, and is thereby retained by the membrane or filter.

The term "biomass" or "biomass feedstock" refers to any material comprising lignocellulosic material. Lignocellulosic materials are composed of three main components: cellulose, hemicellulose, and lignin Cellulose and hemicellulose contain carbohydrates including polysaccharides and oligosaccharides, and can be combined with additional components, such as protein and/or lipid. Examples of biomass include agricultural products such as grains, e.g., corn, wheat and barley; sugarcane; corn stover, corn cobs and other inedible waste parts of food plants; food waste; grasses such as switchgrass; and forestry biomass, such as wood, paper, board and waste wood products.

The term "lignocellulosic" refers to material comprising both lignin and cellulose, and may also contain hemicellulose.

The term "cellulosic," in reference to a material or composition, refers to a material comprising cellulose.

The term "saccharification" refers to production of fermentable sugars from biomass or biomass feedstock. Saccharification can be accomplished by hydrolytic enzymes and/or auxiliary proteins, including, but not limited to, peroxidases, laccases, expansins and swollenins The term "fermentable sugar" refers to a sugar that can be converted to ethanol or other products such as butanols, propanols, succinic acid, and isoprene, during fermentation, for example during fermentation by yeast. For example, glucose is a fermentable sugar derived from hydrolysis of cellulose, whereas xylose, arabinose, mannose and galactose are fermentable sugars derived from hydrolysis of hemicellulose.

The term "simultaneous saccharification and fermentation" (SSF) refers to providing saccharification enzymes during the fermentation process. This is in contrast to the term "separate hydrolysis and fermentation" (SHF) steps.

The term "pretreatment" refers to treating the biomass with physical, chemical or biological means, or any combination thereof, to render the biomass more susceptible to hydrolysis, for example, by saccharification enzymes. Pretreatment can comprise treating the biomass at elevated pressures and/or elevated temperatures. Pretreatment can further comprise physically mixing and/or milling the biomass in order to reduce the size of the biomass particles. Devices that are useful for physical pretreatment of biomass include, e.g., a hammermill, shear mill, cavitation mill or colloid or other high-shear mill. An exemplary colloid mill is the Cellunator™ (Edeniq, Visalia, Calif.). Reduction of particle size is described in, for example, WO2010/025171, which is incorporated by reference herein in its entirety.

The term "pretreated biomass" refers to biomass that has been subjected to pretreatment to render the biomass more susceptible to hydrolysis.

The term "elevated pressure," in the context of a pretreatment step, refers to a pressure above atmospheric pressure (e.g., 1 atm at sea level) based on the elevation, for example at least 20, 30, 40, 50, 60, 70, 80, 90, 100, 110, 120, 130, 140, or 150 psi or greater at sea level.

The term "elevated temperature," in the context of a pretreatment step, refers to a temperature above ambient temperature, for example at least 100, 110, 120, 130, 140, 150, 160, 170, 180, 190, or 200 degrees C. or greater. When used in HPHT pretreatment, the term includes temperatures sufficient to substantially increase the pressure in a closed system. For example, the temperature in a closed system can be increased such that the pressure is at least 100 psi or greater, such as 110, 120, 130, 140, 150 psi or greater.

The term "hydrolysis" refers to breaking the glycosidic bonds in polysaccharides to yield simple monomeric and/or oligomeric sugars. For example, hydrolysis of cellulose produces the six carbon (C6) sugar glucose, whereas hydrolysis of hemicellulose produces the five carbon (C5) sugars xylose and arabinose. Hydrolysis can be accomplished by acid treatment or by enzymes such as cellulase, β-glucosidase, and xylanase. Examples of hydrolytic enzymes include cellulases and hemicellulases. Cellulase is a generic term for a multi-enzyme mixture including exo-cellobiohydrolases, endoglucanases and β-glucosidases which work in combination to hydrolyze cellulose to cellobiose and glucose.

The term "inhibitor" refers to a compound that inhibits the saccharification and/or fermentation process. For example, both cellobiose and glucose inhibit the activity of cellulase enzymes. For example, xylo-oligomers, xylanase inhibitor proteins (XIP), and xylose inhibit the activity of hemicellulases. Other inhibitors include sugar degradation products that result from pretreatment of lignocellulose and/or cellulose. Examples of other inhibitors include 2-furoic acid, 5-hydroxy methyl furfural (HMF), furfural, 4-hydroxybenzoic acid (HBA), syringic acid, vanillin, syringaldehyde, p-coumaric acid, ferulic acid, organic acids such as acetic acid, and phenolic compounds from the breakdown of lignin. These inhibitors can also inhibit fermentation by inhibiting the activity of yeast.

DETAILED DESCRIPTION OF THE INVENTION

Introduction

Figure 1:
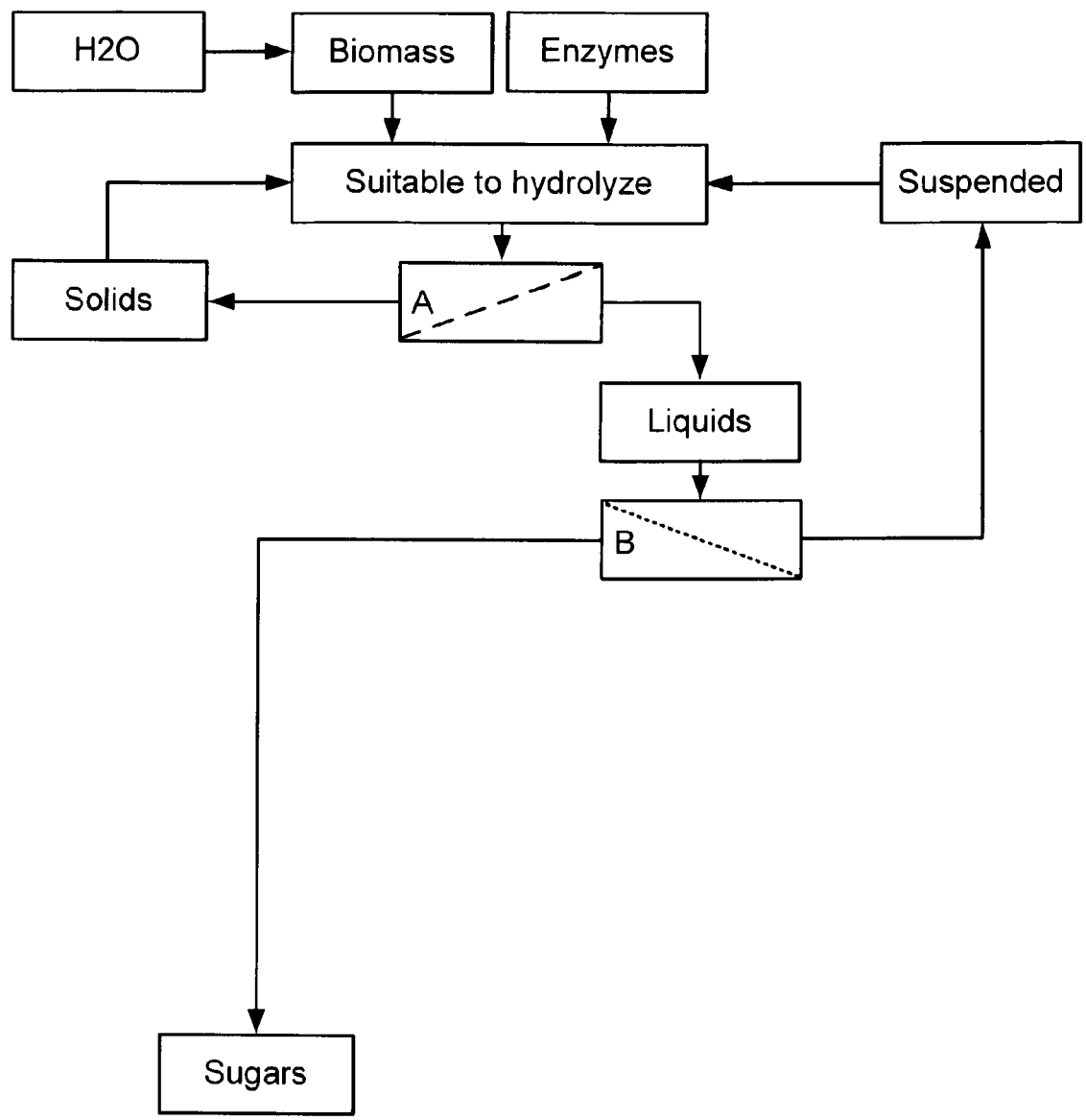
FIG. 1 shows a schematic diagram of one embodiment of the invention, described more fully herein.
Figure 1:
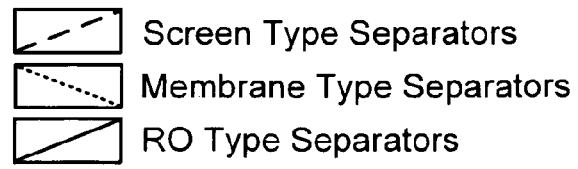

The present invention provides methods and systems for treating lignocellulosic biomass to produce useful products such as carbohydrates and fermentable sugars. The methods and systems provide increased yields of carbohydrates and fermentable sugars by combining enzyme recycling with removal of saccharification enzyme inhibitors and increased solids loading. The methods and systems of the invention will now be described.

I. Methods

In one aspect, the invention provides methods for generating sugar from biomass by contacting the biomass with cellulosic enzymes under conditions in which the biomass is hydrolyzed to a mixture comprising solids, liquids and sugars. The mixture of solids, liquids and sugars is sometimes referred to in the art as a "hydrolyzate." The mixture of solids, liquids and sugars, once formed, is separated into a liquid phase and a solids phase. The liquid phase typically contains sugars and other dissolved solids from the hydrolyzate. The solids phase contains undissolved solids (e.g., suspended solids), cellulosic enzymes that are adsorbed to the solids, and typically also contains residual sugars that were not separated into the liquid phase. In some embodiments, following separation from the liquid phase, the solids phase is subjected to one or more additional hydrolysis steps, such that the solids phase is allowed to incubate under conditions suitable for hydrolysis of the solids phase to sugars. Suitable conditions for hydrolysis of the solids phase to sugars are described below. The sugars that are produced by this additional hydrolysis step can be used for any desired downstream process, such as fermentation to ethanol.

The inventors have discovered that sugars in the solids phase can inhibit further hydrolysis. Accordingly, in some embodiments, prior to further hydrolysis steps, the solids phase is washed to remove at least a portion of the sugars. Washing the solids phase can include contacting the solids phase with an aqueous solution, such as water or a recycled process stream, thereby removing at least a portion (e.g., at least 5%, 10%, 20%, 30%, 40%, 50%, 60%, 70%, 80%, 90%, 95% or more) of the sugars. Washing the solids phase typically results in an aqueous slurry that is referred to as a "washed solids phase." The washed solids phase can be further separated into a liquid and solids. The liquid from the washed solids phase typically comprises sugars that can inhibit the saccharification process. The solids will contain adsorbed enzymes that can be recycled and combined with additional biomass under conditions wherein the biomass is converted to sugars, thereby increasing the saccharification efficiency. In some embodiments, additional enzymes can be added to the biomass and/or solids phase to increase the saccharification efficiency.

The liquid phase can be separated into a permeate comprising dissolved solids and sugars from the hydrolyzate, and a retentate comprising undissolved solids, enzymes, and residual sugars. The retentate can be combined with the biomass and/or the solids phase in order to recycle the enzymes present in the retentate and thus increase the usefulness of the enzymes. Thus, the enzymes and the undissolved solids can be recycled and added back to the biomass during the saccharification step, thereby increasing the enzyme to solids ratio and increasing the saccharification efficiency. The retentate can be combined with unhydrolyzed biomass or partially hydrolyzed biomass as desired. In some embodiments, the retentate is combined with additional untreated biomass under conditions suitable to hydrolyze components of the biomass to sugars.

In some embodiments, the retentate is washed to remove at least a portion of the residual sugars, thereby forming a washed retentate. Removal of the residual sugars is desirable, as sugars can inhibit cellulosic enzymes and thereby decrease the saccharification efficiency. In some embodiments, the washed retentate comprises less than about 10%, 9%, 8%, 7%, 6%, 5%, 4%, 3%, 2% or 1% weight/volume of sugars. The washed retentate can then be combined with biomass and/or solids phase under conditions suitable to convert the biomass and/or solids phase to sugars, or under conditions wherein the biomass or solids phase is converted to sugars.

In some embodiments, the washed retentate is further separated into a liquid comprising sugars and solids comprising enzymes. The solids comprising the enzymes can be recycled back into the biomass feedstock to provide additional enzymes and hydrolysable solids, thereby increasing the overall efficiency of the saccharification process. In one embodiment, the washed retentate is separated using a filter or membrane into a permeate and a retentate. Examples of suitable filters and membranes are described below.

The timing and conditions of the saccharification step can be adjusted such that the biomass is partially hydrolyzed to varying degrees prior to the first or any subsequent separation step, such that complete conversion of the biomass to fermentable sugars does not occur. For example, about 10%, 20%, 30%, 40%, 50%, 60%, 70% or 80% by weight of the starting biomass can be hydrolyzed. Varying the degree of hydrolysis allows control over the amount of enzymes that are released from the lignocellulosic components of the biomass, and thus the amount of enzymes that are recycled with the solids phase.

In some embodiments, the hydrolysis is performed in a reaction vessel. In some embodiments, the reaction vessel is a mixing device. In one embodiment, the reaction vessel is an auger. In some embodiments, the hydrolysis reaction occurs under conditions of counter-current flow, such that the solids are transported in a different or opposite direction than the liquids. Counter-current flow has the advantage of separating liquids containing sugars from the unhydrolyzed solids, thereby lowering the local concentration of sugars that can inhibit hydrolytic enzymes. In one embodiment, the counter-current flow occurs in an auger.

A. Pretreatment

Prior to the hydrolysis steps described herein, the biomass can be pretreated to render the lignocellulose and cellulose more susceptible to hydrolysis. Pretreatment includes treating the biomass with physical, chemical or biological means, or any combination thereof, to render the biomass more susceptible to hydrolysis, for example, by saccharification enzymes. Examples of chemical pretreatment are known in the art, and include acid pretreatment and alkali pretreatment.

One example of physical pretreatment includes elevated temperature and elevated pressure. Thus, in some embodiments, pretreatment comprises subjecting the biomass to elevated temperatures and elevated pressure in order to render the lignocellulose and cellulose accessible to enzymatic hydrolysis. In some embodiments, the temperature and pressure are increased to amounts and for a time sufficient to render the cellulose susceptible to hydrolysis. In some embodiments, the pretreatment conditions can comprise a temperature in the range of about 150° C. to about 210° C. The pretreatment temperature can be varied based on the duration of the pretreatment step. For example, for a pretreatment duration of about 60 minutes, the temperature is about 160 degrees C.; for a duration of 30 minutes, the temperature is about 170 degrees C.; for a duration of 5 minutes, the temperature is about 210 degrees C.

The pretreatment conditions can also comprise increased pressure. For example, in some embodiments, the pressure can be at least 100 psi or greater, such as 110, 120, 130, 140, 150, 200, 265 psi or greater. In some embodiments, the biomass is pretreated in a closed system, and the temperature is increased in an amount sufficient to provide the desired pressure. In one embodiment, the temperature is increased in the closed system until the pressure is increased to about 125, to about 145 psi, or to about 265 psi. Persons of skill in the art will understand that the temperature increase necessary to increase the pressure to the desired level will depend on various factors, such as the size of the closed system and the equilibrium of saturated steam. In some embodiments, pretreatment comprises any other method known in the art that renders lignocellulose and cellulose more susceptible to hydrolysis, for example, acid treatment, alkali treatment, and steam treatment, or combinations thereof.

In some embodiments, the pretreatment step does not result in the production of a substantial amount of sugars. For example, in some embodiments, pretreatment results in the production of less than about 10%, 5%, 1%, 0.1%, 0.01%, or 0.001% by weight glucose, less than about 10%, 5%, 1%, 0.1%, 0.01%, or 0.001% by weight xylose, and/or less than about 10%, 5%, 1%, 0.1%, 0.01%, or 0.001% by weight sugars in general. In some embodiments, the amount of sugars in the process stream entering the pretreatment stage is substantially the same as the amount of sugars in the process stream exiting the pretreatment stage. For example, in some embodiments, the difference between the amount of sugars in the process stream entering the pretreatment stage and the amount of sugars exiting the pretreatment stage is less than about 10%, 5%, 1%, 0.1%, 0.01%, or 0.001% by weight.

In some embodiments, pretreatment can further comprise physically mixing and/or milling the biomass in order to reduce the size of the biomass particles. The yield of biofuel (e.g., ethanol) can be improved by using biomass particles having relatively small sizes. Devices that are useful for physical pretreatment of biomass include, e.g., a hammermill, shear mill, cavitation mill or colloid or any other style or configuration of a high shear mill. Thus, in some embodiments, the pretreatment step comprises physically treating biomass with a colloid mill. An exemplary colloid mill is the Cellunator™ (Edeniq, Visalia, Calif.). In some embodiments, the biomass is physically pretreated to produce particles having a relatively uniform particle size of less than about 1600 microns. For example, at least about 50%, 60%, 70%, 80%, 85%, 90%, or 95% of the pretreated biomass particles can have a particle size from about 100 microns to about 800 microns. In some embodiments, at least about 50%, 60%, 70%, 80%, 85%, 90%, or 95% of the pretreated biomass particles have a particle size from about 100 microns to about 500 microns. In some embodiments, the biomass is physically pretreated to produce particles having a relatively uniform particle size using a colloid mill. The use of a colloid mill to produce biomass particles having a relatively uniform particle size, e.g., from about 100 microns to about 800 microns, can result in increased yield of sugars, as described in U.S. Pat. No. 8,563,282 and Application Publication 2010/0055741 (Galvez et al.), which are incorporated by reference herein in their entirety.

In some embodiments, the pretreatment step does not involve the use of acids which can degrade sugars into inhibitors of fermentation.

In some embodiments, the pH of the pretreated biomass is adjusted to a pH of between about 3.0 and about 6.5. In some embodiments, the pH of the biomass is adjusted during or after the pretreatment step to be within the optimal range for activity of saccharification enzymes, e.g., within the range of about 4.0 to 6.0. In some embodiments, the pH of the biomass is adjusted using $Mg(OH)_2$, $NH_4OH$, $NH_3$, or a combination of $Mg(OH)_2$ and $NH_4OH$ or $NH_3$.

After pretreatment, the pretreated biomass is hydrolyzed to produce sugars using the methods described herein. Non-limiting embodiments will now be described.

B. Exemplary Methods for Generating Sugar From Biomass

Referring now to FIG. 1, one embodiment will be described. A lignocellulosic biomass is contacted with an aqueous solution such as water and enzymes under conditions suitable to hydrolyze at least a portion of the biomass to sugars. The biomass can be an aqueous slurry. The slurry can have, for example, a solids content of at least about 1%, 5%, 10%, 15%, 20%, 25%, or 30% weight by volume. The biomass can be hydrolyzed to various degrees of saccharification depending on factors such as the amount of solids to be recycled. After the biomass is hydrolyzed the hydrolyzed biomass is separated into a solid phase and a liquid phase. The separation can be accomplished using, for example, a screen type separator (A). Examples of screen type separators include screens, vibrating screens, pressure screens, reciprocating screens (rake screens), gyratory screens/sifters, as described further herein. Other separation methods can also be used, for example, a press, a centrifuge, a settling tank, or other suitable separation device can be employed. In some embodiments, the solid phase is recombined with the biomass and undergoes further saccharification to produce more sugars.

As shown in FIG. 1, the liquids phase can be further separated into a retentate comprising solids and enzymes and a permeate comprising dissolve compounds such as sugars and residual dissolved enzymes not associated with the solids. This separation can be accomplished, for example, using a filter or membrane type separator (B). Examples of membrane type separators include ultrafiltration (UF) membranes, microfiltration (MF) membranes, reverse osmosis (RO) membranes, and/or any other membrane type, and the membrane type separator can be configured as a Tangential Flow Filtration (TFF) system, cross flow, counter flow, tube bundle, rolled assembly, and stacked plate system. The membrane surfaces can be passive or have ionic charged surfaces and can be single or multiple layers of similar or different materials. As shown in FIG. 1, the retentate is recycled and combined with the biomass, wherein the biomass undergoes further saccharification and is converted to additional sugars. The permeate comprising sugars can be used for any desired downstream or upstream process. For example, the sugars can be fermented to produce biofuels such as ethanol or can be used for generating other products. The liquid and solid phase separation can be conducted with any combination of membranes and modules, for example the liquid phase separation can be first treated with a screen separator followed by the fine membrane separation to enhance the throughput and operability of the process. The retentate of both processes can be combined as a single retentate. The permeate of the first process is used as the feed material for the following process with the permeate of the final process becoming the permeate comprising sugars.

As is apparent from FIG. 1, the method is a continuous process wherein solids, including solids with enzymes adsorbed thereon, are recycled and combined with biomass in the saccharification step. The solids recovered in the retentate from the liquid phase are also recycled and combined with biomass in the saccharification step. However, it will be understood that the methods described herein can be performed in a batch process or a fed batch process as well.

Figure 2:
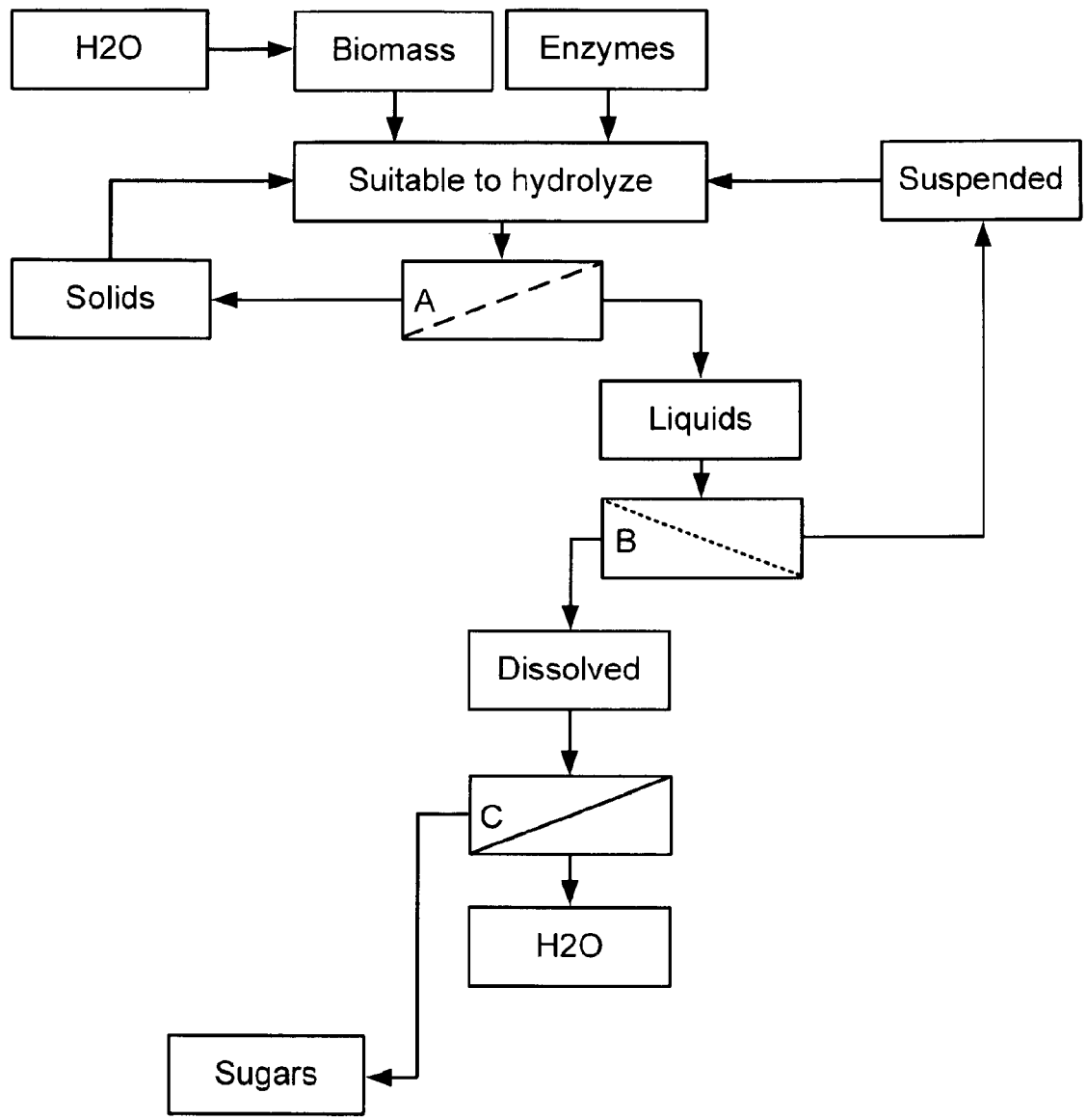
FIG. 2 shows a schematic diagram of one embodiment of the invention, described more fully herein.

Referring now to FIG. 2, another embodiment will be described. As described above for FIG. 1, the lignocellulosic biomass is contacted with an aqueous solution such as water and enzymes under conditions suitable to hydrolyze at least a portion of the biomass to sugars. The hydrolyzed biomass is separated into a solids phase and liquid phase (A), as described above. The solids phase is recycled back into contact with the biomass, wherein additional saccharification occurs. The liquid phase is separated into a retentate comprising solids and a permeate comprising sugars (B). The retentate is recycled back into contact with the biomass, wherein additional saccharification occurs.

In the embodiment described in FIG. 2, the dissolved sugars in the permeate are further separated into a concentrated sugar stream and an aqueous stream. The separation can be accomplished by a reverse osmosis type separator (C). Examples of reverse osmosis type separators are described below. The concentrated sugar stream can be used for any desired purpose, for example, it can be fermented to produce ethanol.

Figure 3:
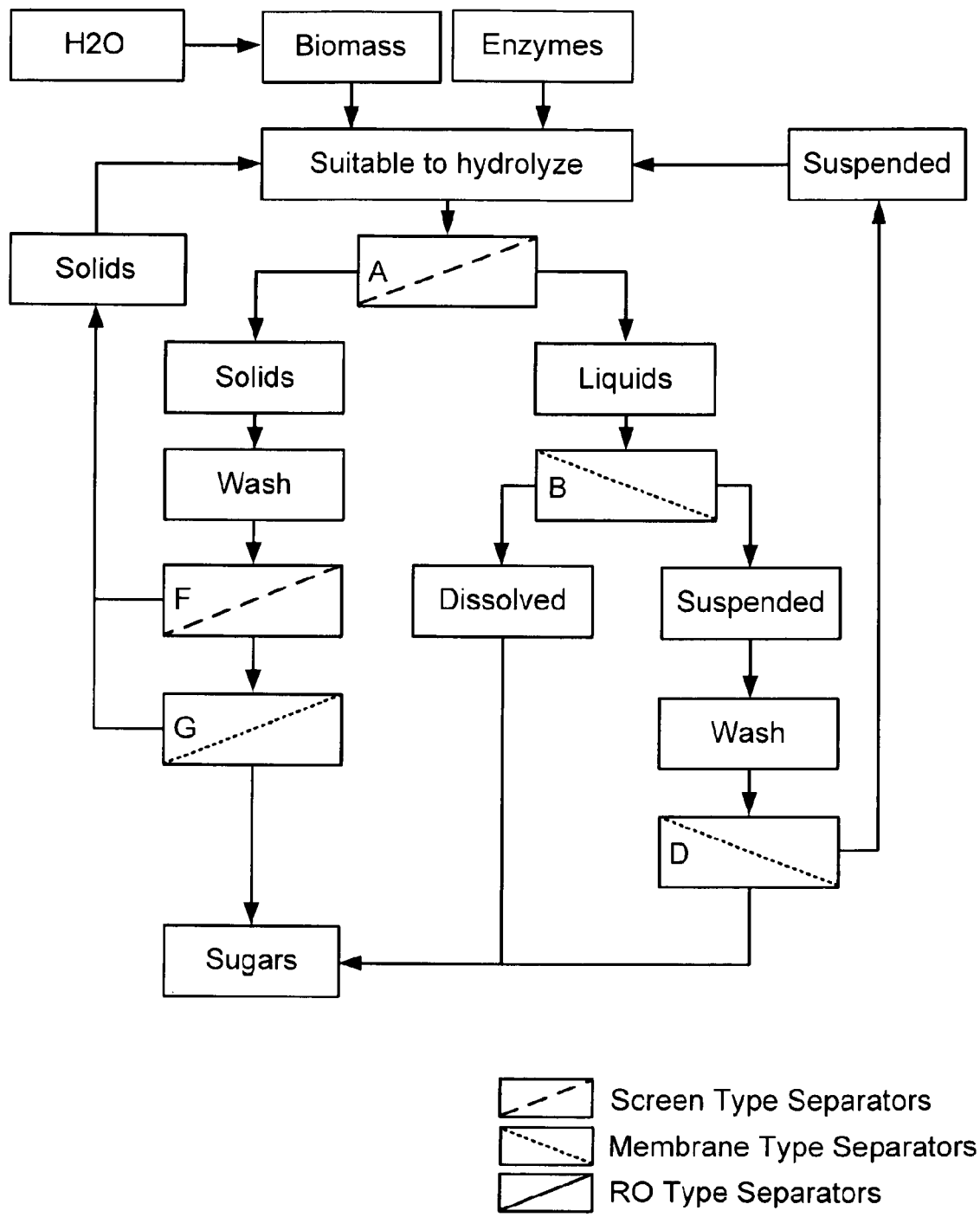
FIG. 3 shows a schematic diagram of one embodiment of the invention, described more fully herein.

Referring now to FIG. 3, another embodiment will be described. As described above for FIG. 1, the lignocellulosic biomass is contacted with an aqueous solution such as water and enzymes under conditions suitable to hydrolyze at least a portion of the biomass to sugars. The hydrolyzed biomass can be separated into a solids phase and liquid phase (A), as described above. In some embodiments, the solids phase is recycled back into contact with the biomass, wherein additional saccharification occurs. The liquid phase can then be separated into a retentate comprising solids and a permeate comprising sugars (B). In some embodiments, the retentate is recycled back into contact with the biomass, wherein additional saccharification occurs. The sugars in the permeate can be used for any desired purpose, including fermentation to produce ethanol.

In the embodiment shown in FIG. 3, the solids from the retentate are re-suspended and washed to produce a washed retentate. The washed retentate can then be separated into a second permeate and a second retentate. The separation can be accomplished using a membrane type Separator (D). Examples of membrane type separators are described below. In some embodiments, the second retentate is recycled and combined with the biomass and/or the solids phase to undergo further saccharification. The second permeate comprises sugars that can be used in downstream processes such as fermentation.

As further shown in the embodiment illustrated in FIG. 3, the solid phase can be washed and separated into a filtrate and a third retentate. The separation can be accomplished using a screen type Separator (F), as described herein. The retentate comprises solids and enzymes, and can be recycled into contact with the biomass or solids phase to undergo further saccharification. The filtrate can then be further separated into a third permeate and fourth retentate. The separation can be accomplished using a membrane type Separator (G), as described herein. The permeate comprises sugars that that can be used in downstream processes such as fermentation.

Figure 4:
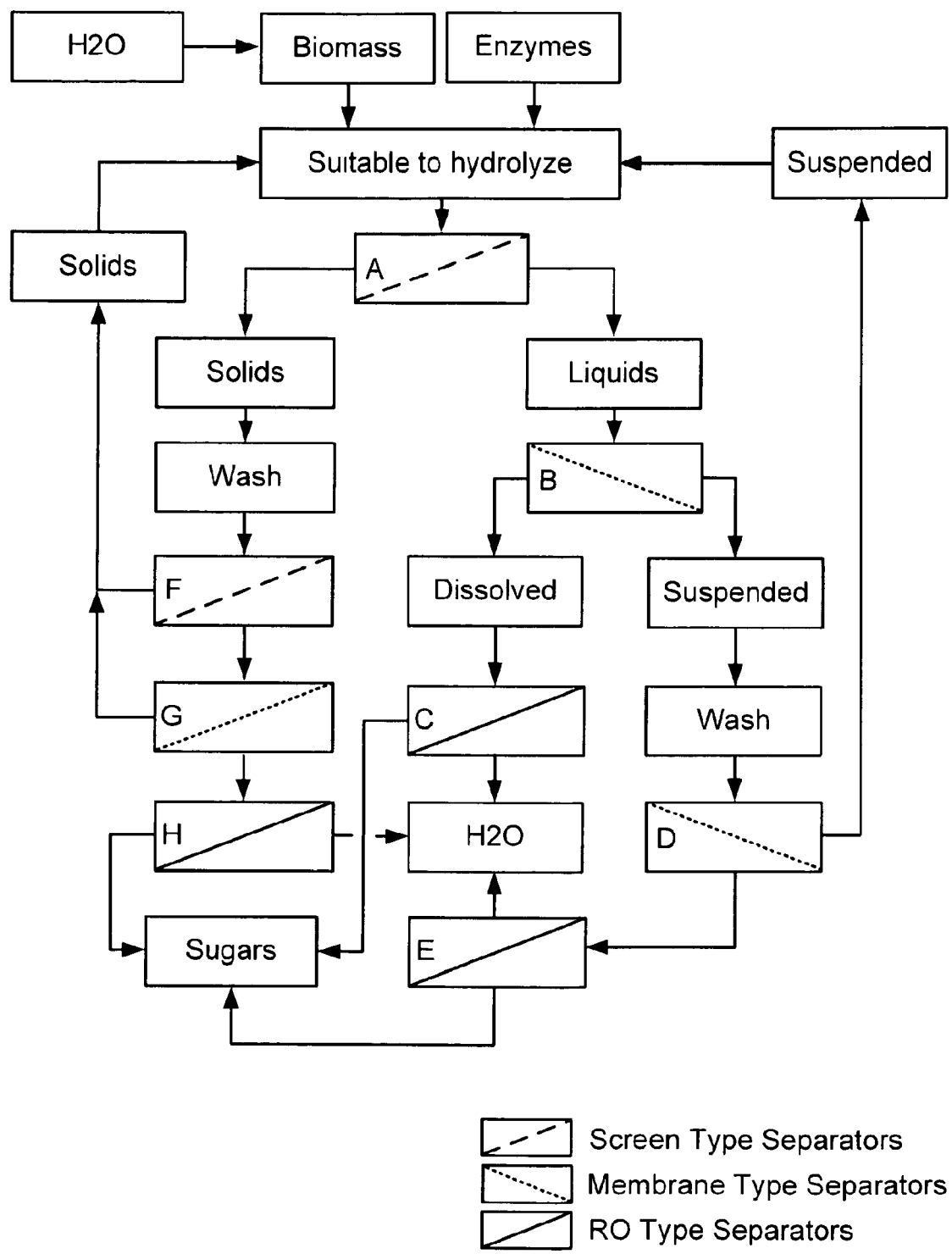
FIG. 4 shows a schematic diagram of one embodiment of the invention, described more fully herein.

Referring now to FIG. 4, another embodiment will be described. As described above for FIG. 3, the lignocellulosic biomass is contacted with an aqueous solution such as water and enzymes under conditions suitable to hydrolyze at least a portion of the biomass to sugars. The hydrolyzed biomass can be separated into a solids phase and liquid phase (A), as described above. In some embodiments, the solids phase is recycled back into contact with the biomass, wherein additional saccharification occurs. The liquid phase can be separated into a retentate comprising solids and a permeate comprising sugars (B). In some embodiments, the retentate is recycled back into contact with the biomass, wherein additional saccharification occurs. The sugars in the permeate can be used for any desired purpose, including fermentation to produce ethanol.

As shown in the embodiment illustrated in FIG. 4, the permeate from separation step (B) comprising dissolved sugars can be separated into a concentrated sugar stream and an aqueous stream. In some embodiments, the permeate from separation step (G) is further separated into a concentrated sugar stream and an aqueous stream. The permeate from separation step (D) can be further separated into a concentrated sugar stream and an aqueous stream. In one non-limiting embodiment, the separation to produce a concentrated sugar stream is accomplished by a reverse osmosis type separator (C), as described herein. The concentrated sugar stream can be used for any desired purpose, for example, it can be fermented to produce ethanol.

In some embodiments, the saccharification step can be performed in a mixing device that mixes the biomass slurry comprising enzymes. For example, in some embodiments, saccharification step can be performed in an auger. In some embodiments, the saccharification step is performed under conditions of counter-current flow, wherein the solids are transported in an opposite direction to the liquids in the slurry.

One advantage of the methods described herein is the removal of inhibitors of saccharification enzymes. For example, glucose inhibits cellulases and XIP, xylo-oligomers, and xylose inhibit hemicellulases. In particular, by separating the liquids comprising inhibitory sugars from the solids early during the hydrolysis process, the glucose concentration is reduced to levels that do not inhibit enzymes, and hydrolysis of the solids can continue in the absence of inhibitory glucose concentrations. The solids phase can also be washed to remove sugars and other inhibitors, as described above.

Another advantage of the methods described herein is that the yield of sugars and therefore ethanol from biomass can be increased without having to increase the solids concentration to undesired levels. For example, saccharification of a high solids concentration of biomass should produce more sugars in a given volume of liquid. However, at solids concentrations above 30% w/v, the solids are difficult to transport within the ethanol production facility. Thus, in the instant methods, the high concentration solids can be diluted with an aqueous liquid to produce a slurry with lower solids concentration, which has the added advantage of diluting inhibitory sugars. The slurry can be pressed to remove a majority of the liquid and dissolved inhibitory sugars, and the solids (press-cake) added back to biomass for further saccharification. The net effect is increased yield of sugars without the disadvantages associated with high solids concentrations.

C. Separation Methods

The methods described herein make use of various types of separators and separation methods. In some embodiments, the separator is a screen type separator. Non-limiting examples of screen type separators include screens, vibrating screens, reciprocating screens (rake screens), gyratory screens/sifters, and pressure screens.

In some embodiments, the separator is a membrane type separator. Examples of membrane type separators include ultrafiltration (UF) membranes, microfiltration (MF) membranes, reverse osmosis (RO) membranes, or any other membrane type, and the membrane type separator can be configured as a Tangential Flow Filtration (TFF) system, cross flow, counter flow, tube bundle, rolled assembly, spiral rolled, and stacked plate system. The membrane surfaces can be passive or have ionic charged surfaces and can be single of multiple layers of similar or different materials.

MF membranes typically have a pore size of between 0.1 micron and 10 microns. Examples of microfiltration membranes include glass microfiber membranes such as Whatman GF/A membranes. UF membranes have smaller pore sizes than MF membranes, typically in the range of 0.001 to 0.1 micron. UF membranes are typically classified by molecular weight cutoff (MWCO). Examples of ultrafiltration membranes include polyethersulfone (PES) membranes having a low molecular weight cutoff, for example about 10 kDa. UF membranes are commercially available, for example from Synder Filtration (Vacaville, Calif.).

Filtration using either MF or UF membranes can be employed in direct flow filtration (DFF) or Tangential Flow Filtration (TFF). DFF, also known as dead end filtration, applies the feed stream perpendicular to the membrane face such that most or all of the fluid passes through the membrane. TFF, also referred to as cross-flow filtration, applies the feed stream parallel to the membrane face such that one portion passes through the membrane as a filtrate or permeate whereas the remaining portion (the retentate) is recirculated back across the membrane or diverted for other uses. TFF filters include microfiltration, ultrafiltration, nanofiltration and reverse osmosis filter systems. The cross-flow filter may comprise multiple filter sheets (filtration membranes) in a stacked arrangement, e.g., wherein filter sheets alternate with permeate and retentate sheets. The liquid to be filtered flows across the filter sheets, and solids or high-molecular-weight species of diameter larger than the filter sheet's pore size(s), are retained and enter the retentate flow, whereas the liquid along with any permeate species diffuse through the filter sheet and enter the permeate flow. The TFF filter sheets, including the retentate and permeate sheets, may be formed of any suitable materials of construction, including, for example, polymers, such as polypropylene, polyethylene, polysulfone, polyethersulfone, polyetherimide, polyimide, polyvinylchloride, polyester, etc.; nylon, silicone, urethane, regenerated cellulose, polycarbonate, cellulose acetate, cellulose triacetate, cellulose nitrate, mixed esters of cellulose, etc.; ceramics, e.g., oxides of silicon, zirconium, and/or aluminum; metals such as stainless steel; polymeric fluorocarbons such as polytetrafluoroethylene; and compatible alloys, mixtures and composites of such materials. Cross-flow filter modules and cross-flow filter cassettes useful for such filtration are commercially available from SmartFlow Technologies, Inc. (Apex, N.C.). Suitable cross-flow filter modules and cassettes of such types are variously described in the following United States patents: U.S. Pat. Nos. 4,867,876; 4,882,050; 5,034,124; 5,034,124; 5,049, 268; 5,232,589; 5,342,517; 5,593,580; and 5,868,930; the disclosures of all of which are hereby incorporated herein by reference in their respective entireties.

In some embodiments, the separator is a reverse osmosis (RO) type separator. Examples of RO type separators include RO spiral membranes available from Koch Membrane Systems (Wilmington, Mass.) or Synder Filtration (Vacaville, Calif.).

D. Saccharification and Fermentation Conditions

The saccharification reaction can be performed at or near the temperature and pH optimum for the saccharification enzymes used. In some embodiments of the present methods, the temperature optimum for saccharification ranges from about 15 to about 100° C. In other embodiments, the temperature range is about 20 to 80° C., about 35 to 65° C., about 40 to 60° C., about 45 to 55° C., or about 45 to 50° C. The pH optimum for the saccharification enzymes can range from about 2.0 to 11.0, about 4.0 to 6.0, about 4.0 to 5.5, about 4.5 to 5.5, or about 5.0 to 5.5, depending on the enzyme.

Examples of enzymes that are useful in saccharification of lignocellulosic biomass include glycosidases, cellulases, hemicellulases, starch-hydrolyzing glycosidases, xylanases, ligninases, and feruloyl esterases, and combinations thereof. Glycosidases hydrolyze the ether linkages of di-, oligo-, and polysaccharides. The term cellulase is a generic term for a group of glycosidase enzymes which hydrolyze cellulose to glucose, cellobiose, and other cello-oligosaccharides. Cellulase can include a mixture comprising exo-cellobiohydrolases (CBH), endoglucanases (EG) and β-glucosidases (βG). Specific examples of saccharification enzymes include carboxymethyl cellulase, xylanase, β-glucosidase, β-xylosidase, and α-L-arabinofuranosidase, and amylases. Saccharification enzymes are commercially available, for example, Pathway™ (Edeniq, Visalia, Calif.), Cellic® CTec2 and HTec2 (Novozymes, Denmark), Spezyme® CP cellulase, Multifect® xylanase, and Trio® (Genencor International, Rochester, N.Y. Saccharification enzymes can also be expressed by host organisms, including recombinant microorganisms.

The enzyme saccharification reaction can be performed for a period of time from about several minutes to about 250 hours, or any amount of time between. For example, the saccharification reaction time can be about 5 minutes, 10 minutes, 30 minutes, 60 minutes, or 2, 4, 6, 8, 12, 16, 18, 24, 36, 48, 60, 72, 84, 96, 108, 120, 130, 140, 150, 160, 170, 180, 190, 200, 210, 220, 230, 240 or 250 hours. In other embodiments, the saccharification reaction is performed with agitation to improve access of the enzymes to the cellulose.

The amount of saccharification enzymes added to the reaction can be adjusted based on the cellulose content of the biomass and/or the amount of solids present in a composition comprising the biomass, and also on the desired rate of cellulose conversion. For example, in some embodiments, the amount of enzymes added is based on percent by weight of cellulose present in the biomass, as specified by the enzyme provider(s). The percent of enzyme added by weight of cellulose in such embodiments can range, for example, from about 0.1% to about 10% on this basis.

After the biomass is pretreated and hydrolyzed as described herein, the sugars can be used for any desired downstream process or refined as a product. In one embodiment, the sugars are fermented to ethanol, as described below.

After the saccharification steps described above, the treated biomass and/or converted sugars can be subjected to fermentation under conditions sufficient to produce ethanol from the sugars. The fermentation conditions include contacting the biomass and/or sugars with yeast that are capable of producing ethanol from sugars. If desired, the biomass can be subjected to simultaneous saccharification and fermentation (SSF). The pH of the SSF reaction can be maintained at the optimal ranges for the activity of the Cellulosic enzymes, for example between about 4.0 and 6.0, or between about 4.5 and 5.0.

II. Systems

In another aspect, the invention provides systems suitable for performing the methods described herein for generating sugar from biomass. In one embodiment, the system comprises a mixing device that is capable of mixing biomass, typically as a biomass slurry, and transporting the biomass solids within the device. In one embodiment, the mixing device is capable of transporting the solids in one direction and the liquids in another or opposite direction within the device. In one embodiment, the mixing device is an auger. In some embodiments, the system comprises 2 or more mixing devices in fluid communication, for example, 2, 3, 4, or more mixing devices in fluid communication.

Thus, in one embodiment, the system comprises a first auger having a solids inlet and a screw inside the auger to direct a solid mass in the auger from the first end to the second end of the auger. The auger can also have a liquid outlet at the first end, a solids outlet at the second end, and a separator suitable for separating the biomass into a liquid phase and a solids phase. The separator is positioned between the liquid outlet and the screw and the solids outlet. The system further comprises a second auger having an inlet in fluid communication with the solids outlet (of the first auger), the inlet configured for receiving the solids mass from the first auger. The second auger also has a solids outlet.

In some embodiments, a second, third, fourth or more mixing device, which can be augers or other devices, can be integrated in series or parallel configurations. In some embodiments when the mixing device has a separate liquid outlet and solids outlet, the solids outlet can feed the solids inlet to the next mixing device in the system. In some embodiments, the mixing device has one, two or more liquid inlet connections positioned along the device between the first end and the second end. In some embodiments, the liquid inlet connection is positioned near the solid outlet or second end. In some embodiments, the liquid outlet of one device feeds into one of these liquid inlet connections (i.e., the liquid outlet of one device is in fluid communication with the liquid inlet connection). In one embodiment, the liquid output of all the mixing devices is combined, further processed and returned to the liquid inlet of one or more devices. In some embodiments the liquid outlet of the last mixing device is in fluid communication with the liquid inlet of the next to the last device, such that multiple devices effectively have counter flow of liquid and solids throughout a system with multiple mixing devices. The process liquid removed from the liquid outlet may or may not be further processed before being returned into a liquid inlet of the same or different mixing devices. Any combination of fluid communications of the various liquid inlets and liquid outlets between multiple devices are envisioned and those illustrated are representative of some embodiments.

In one embodiment, the screw inside the auger transports the solids mass and the liquids in the same direction, resulting in direct flow within the auger. In some embodiments, the screw inside the auger transports the solids mass in a direction opposite that of liquid flow inside the auger, thereby creating a counter-current flow. The advantages of counter current flow increases the efficiency of separating inhibitors of saccharification enzymes in the liquid from the solids that are hydrolyzed by the enzymes. In one embodiment, the first and/or second auger is inclined such that the liquid outlet is lower than the solids outlet, thus facilitating counter-current flow inside the auger. In some embodiments, the screw inside the auger can be a single screw, dual screw, or multiple screw mechanism.

In some embodiments, the system further comprises a second separator suitable for separating the biomass into a liquid phase and a solids phase, the second separator positioned between the solids outlet of the first auger and the inlet of the second auger. The second separator can be in fluid communication with the solids outlet of the first auger and the inlet of the second auger. In some embodiments, the first and/or second separator is a screen, a vibrating screen, or a press. In some embodiments, the second separator can be physically integrated into the mixing device. In some embodiments the liquid outlet stream of the second separator device is in fluid communication with the liquid inlet positioned at the second end of the mixing device.

In some embodiments, the first and/or second separator is in fluid communication with a filter that is suitable for separating the liquid phase into a filtrate and a retentate. In one embodiment, the filter is a microfilter such as a TFF system as described above. The filter can be in fluid communication with the liquid outlet of the first auger and the inlet of the first auger or the inlet of the second auger. In some embodiments, the solids and enzymes in the retentate are recycled and added to the biomass in the first or second auger. The filtrate typically comprises sugars that can be used for downstream processes such as fermentation. The filtrate can be passed through an RO system to further concentrate the sugars, as described above.

Prior to contacting the liquid phase with the filter, for example a TFF microfiltration system, the liquid can be treated with a surfactant such as Tween 20, Tween 80, or polyethylene glycol (PEG) to aid in separating the bound enzymes from the lignin. The system can further include another microfiltration separator to concentrate the recovered enzymes before they are recycled back into the auger to contact additional biomass. If desired, the lignin enriched solids in the retentate can be purged and sent to cogeneration or used as co-products. In some embodiments, the surfactants or other molecules that increase the hydrolysis yield or rate can be recovered and recycled back into contact with additional biomass. This recycling can use any of the various liquid inlet and solids inlet connections of a multiple mixing device system.

The system described herein can be operated in a batch, a fed batch, or a continuous manner. When operating in a continuous manner, the enzymes can be added to the biomass as they travel through the first auger or before the biomass is added to the first auger. Fresh enzymes can also be added at any of the liquid inlets of the various mixing devices in a multiple device system. The biomass solids are moved through the auger for a time and under conditions suitable to achieve the desired degree of hydrolysis (saccharification). The inclination of the augers permits the liquid phase (comprising liquefied biomass) to pass through the first separator, for example, a screen, and drain out of the liquid outlet. In one embodiment, the screen has about 250 micrometer openings. In other embodiments the screen has about 500, or about 400, or about 300, or about 200, or about 100, or about 50, or about 10 micrometer openings. The liquid phase can be passed through the microfiltration system, for example, the TFF system, that permits the dissolved solids and sugars to pass through the filter, while any enzymes and non-dissolved solids are concentrated and returned to the interior of the auger. The filtrate comprising the sugars can be sent to fermentation or concentrated using an RO system or further processed to adjust or improve the quality or characteristics of the sugar stream. Operating the system as describe above permits the volume of liquid moving to each subsequent or downstream auger to be reduced compared to the volume in the previous auger. The reduction in fluid with each downstream auger permits higher throughput for a given volume. Without intending to limit the scope of the invention, this higher throughput is believed to be accomplished by removing the sugars and water from the saccharification part of the process, thus reducing the volume of the solids and liquid mixture, which includes glucan and xylan that are able to be hydrolyzed into glucose and xylose. The reduction in fluid with each downstream auger can also increase the enzyme to solids ratio by recycling the partially depleted solids comprising enzymes back to the auger, thereby recycling the enzymes back into the auger. As described above, the increase in the enzyme-to-solids ratio can also increase the saccharification efficiency compared to a batch process.

In some embodiments, the solids concentration in the first auger is at least about 1%, 5%, or 10% solids weight/volume. The solids concentration can increase to at least about 15%, 20%, 25%, 30%, 35%, 40%, 45%, or 50% w/v, e.g., between about 25% and 35% as the solids move to subsequent augers in the system.

The augers described herein can have additional inlets for adding biomass, solids, and/or enzymes.

In some embodiments, the system further comprises at least one additional auger. The at least one additional auger has a solids inlet in fluid communication with the solids outlet of the first and/or second auger, and a solids outlet. In one embodiment, the at least one additional auger is aligned in series with the first and second augers such that a solid mass is directed through the series of augers. In some embodiments, the solids outlet of at least one of the augers is in fluid communication with a third separator suitable for removing liquids from the treated biomass. The third separator can be a screen, a vibrating screen, a press, or any other device suitable for separating a liquid stream form a slurry stream. For example, the biomass can be passed through a vibrating screen to remove liquids from the solids, and additionally pressed to remove the majority of remaining sugars in the interstitial liquids of the treated biomass. The liquid from the press comprising the sugars can be sent to fermentation or concentrated using an RO system. The pressed solids can be sent to the next auger in the series. The liquid from the press can be put in fluid communication with the liquid inlet for other mixing devices in the system.

Figure 6:
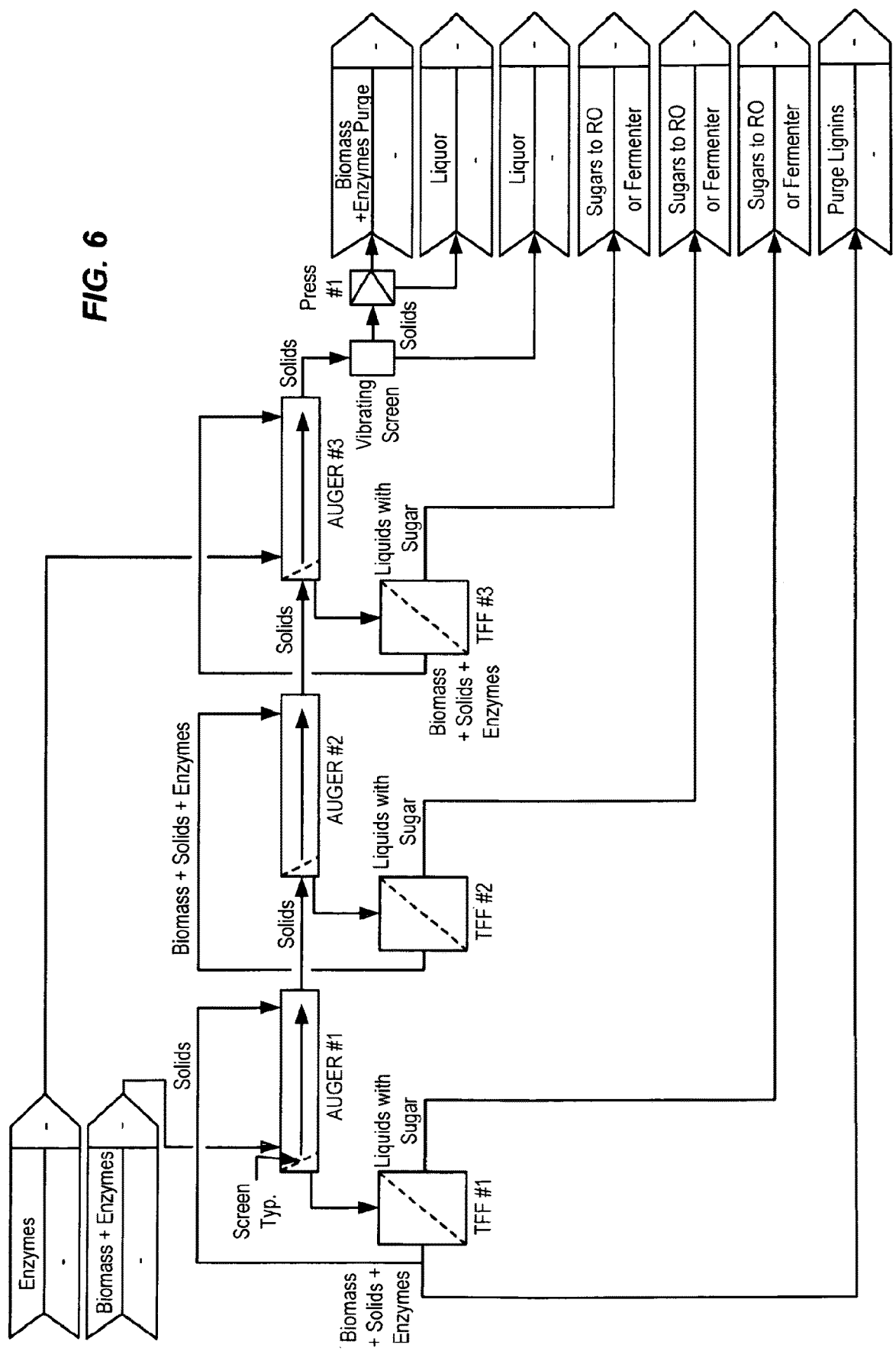
FIG. 6 illustrates one embodiment of a system of the invention, described more fully herein.

Referring now to FIG. 6, one embodiment of the system will be described. A first auger having a first end with a liquid outlet and second end with a solids outlet is in fluid communication with the inlet of a second auger. The biomass and enzymes are added to the auger through the solids inlet. The biomass solids are transported from the solids inlet towards the solids outlet by a motorized screw inside the auger. The biomass solids are hydrolyzed by the enzymes as they are transported from the inlet to the second end of the auger. The auger can be inclined such that the liquids outlet is lower than the solids outlet, thus permitting counter current flow inside the auger. The screw is configured such that the tolerance between the screw threads and the inside of the auger wall permits fluids to pass by the threads but transports the majority of un-hydrolyzed solids towards the solids outlet. The hydrolyzed biomass liquids are passed through a screen and then out of the liquid outlet. The liquids are then passed through a microfiltration TFF system. The solids and enzymes recovered in the retentate of the TFF system are then added back to the first auger. The solids in the retentate can be added to the auger through an inlet near the second end, in order to keep the solids concentration near the second end higher. The filtrate from the TFF system comprises sugars that are sent to fermentation or an RO system for further concentration of sugars.

The solids that exit the solids outlet from the first auger are added to the solids inlet of the second auger. The solids are typically an aqueous slurry. The solids concentration in the second auger can be higher than the solids concentration in the first auger. The solids are then transported by a screw inside the second auger from the inlet to the outlet at the second end. The liquids from the slurry are permitted to pass through a screen located between the screw and the liquid outlet at the first end. The second and subsequent augers can be inclined to facilitate counter-current flow within the auger. The liquid comprising biomass hydrolyzate that exits the liquid outlet can be passed through a microfiltration TFF system, as described above. The solids and enzymes recovered from the TFF system are then added back to the second auger. Alternatively, the concentrated solids and enzymes recovered from the TFF system are then added back to the first auger, thereby permitting counter current flow of concentrated enzymes with respect to solids. This process can be repeated for several augers.

In another embodiment, the auger comprises a plurality of injection ports or liquid inlets that are used for adding enzymes to the auger. The concentration and types of enzymes added to each injection port can differ such that saccharification of the biomass is optimized. The concentration and types of enzymes can vary depending on if the system is operated in direct flow or counter-current flow.

In some embodiments, water or other aqueous solution is added to the augers to wash the solids. The aqueous solution can be either newly added (fresh) or recycled from an internal stream. For example, the permeate from the RO system can be used to wash the biomass. Washing the solids in the augers decreases the sugar concentration, resulting in less inhibition of enzyme activity and increased saccharification efficiency. If the added aqueous solution decreases the sugar concentration below desired levels, the TFF permeate can be fed to an RO system to increase the sugar concentration before fermentation. The permeate from the RO system can then be recycled back to wash more solids.

Figure 7:
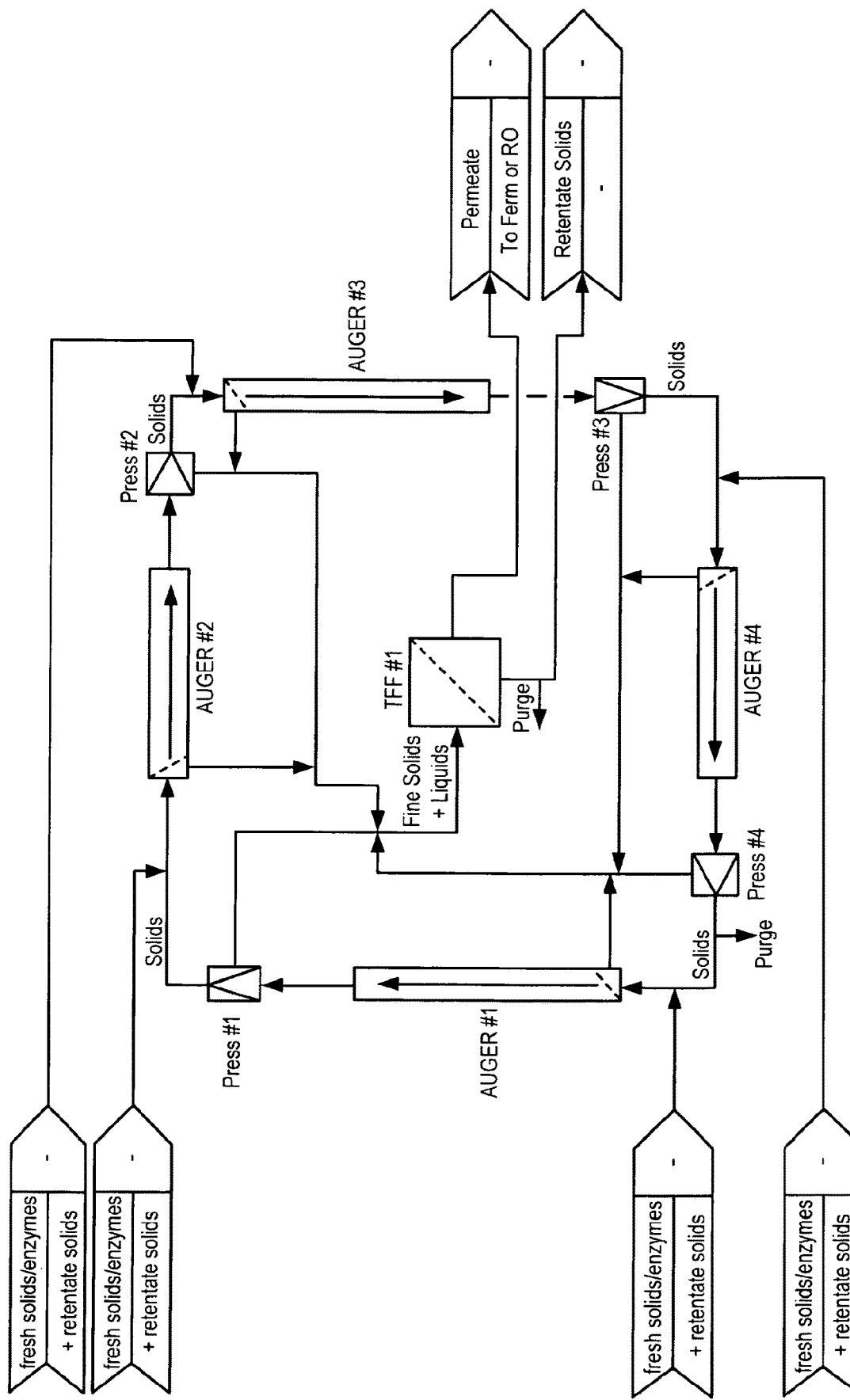
FIG. 7 illustrates another embodiment of a system of the invention, described more fully herein.

Referring now to FIG. 7, another embodiment of the system will be described. FIG. 7 shows a recirculating auger system that is designed to increase the overall solids time while reducing the sugar residence time. The system comprises a plurality of augers that are in fluid communication as described above, except that the last auger is in fluid communication with the first auger. The solids outlet from each auger is in fluid communication with a separation device such as a vibrating screen or a press. The press can have a screen that excludes solid particles over a certain size, for example screen sizes between 40 μm and 510 μm. Screens with these sizes permit the sugars and dissolved lignins or lignin of fine particle sizes to pass through the mesh, while large particles containing glucan and xylan (the parts of the biomass which can be saccharified) are retained. Solids that are too large to pass through the screen and enter the press are sent to the next auger in the series. Alternatively, a vibrating screen can be used to separate the solids from the liquids. The press or vibrating screen is in fluid communication with a TFF system. The pressate liquids are separated by the TFF system as described above. The retentate solids from the TFF system can be recycled and added to fresh biomass and/or purged from the system.

As shown in FIG. 7, fresh solids (biomass) and enzymes can be added to each of the augers in addition to the recycled retentate solids. In one embodiment, fresh solids are not added to one of the augers in the series, which permits additional saccharification time for all the biomass that is resident in this auger. In one embodiment, the solids from the last auger in the recirculating auger system are recycled back to the first auger, where the solids can be contacted with additional biomass for further saccharification. If desired, some or all of the solids can be purged from the system. The solids can be purged from the TFF retentate, from a step between the augers, or after the last auger.

EXAMPLES

The following examples are offered to illustrate, but not to limit the claimed invention.

Example 1

This example demonstrates that washing the solids retained by a filtration membrane results in improved yield of glucose when the washed solids are combined with additional biomass prior to saccharification.

Saccharification of corn stover was performed for 15 hours. The material was passed through a hand sieve. The liquid was concentrated using a TFF system with a 20 kDa membrane. It was found that 40% of the mass of the system could be removed from the system through the filter. The solids were recombined with the TFF retentate and went through saccharification for an additional 24 h. In a separate experiment, the TFF retentate was washed (1×) to remove additional sugars that would inhibit enzyme activity. Then the solids were recombined with the washed TFF retentate and went through saccharification for an additional 24 h.

Figure 5:
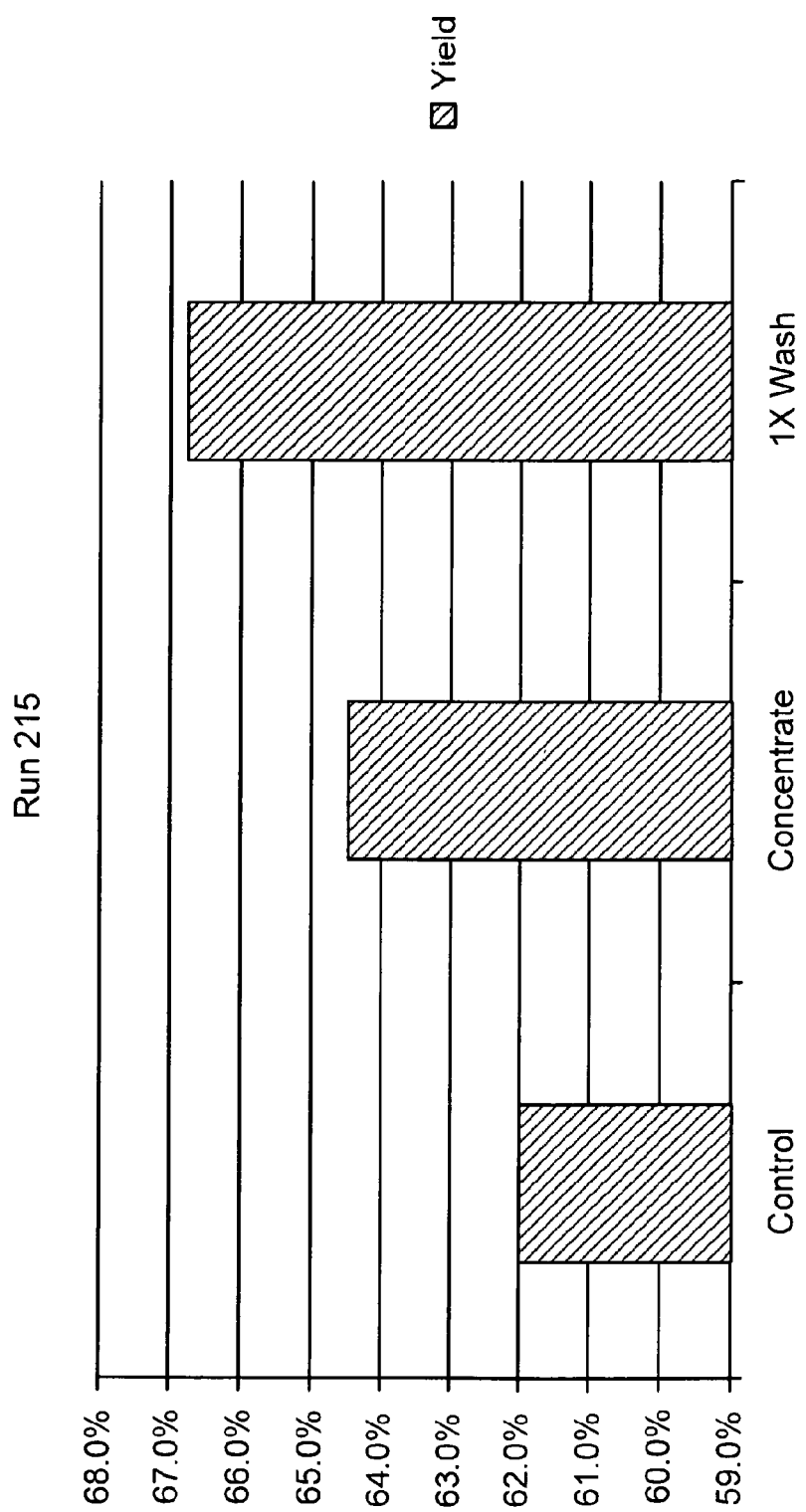
FIG. 5 shows the results from an experiment comparing the yield of glucose from glucan in corn stover that was saccharified for 15 hours then filtered through a hand sieve (control), or concentrated using a TFF system (concentrate), or concentrated and washed TFF retentate (1× washed), as described in the Examples.

FIG. 5 displays the results from the above experiment. Washing the sugar out of the system to reduce its concentration further increased the yield. These results are consistent with a kinetic model that uses first order kinetics for the biomass concentration and a negative term that is first order with the sugar concentration.

This example shows that removal of sugars from partially hydrolyzed solids can increase the yield of sugars in subsequent saccharification steps.

Example 2

This example demonstrates a system for generating sugar from biomass where the enzymes are contacted with biomass in conditions suitable to hydrolyze the biomass into sugars using augers.

In this example, the liquid phase was separated from the solid phase using a screen and a vibrating screen. The liquid was separated using a TFF membrane into a permeate containing sugar and some dissolved solids and a retentate containing enzymes, sugar, and any remaining particulate solids. The retentate was then recombined with the solids in the auger system. The biomass used in this example was corn stover and the system was operated as a 12 hour batch.

In this example, the corn stover biomass was pretreated for 40 minutes at 179° C. The corn stover slurry was transferred into the first of 4 augers at 16% solids. Accellerase® Trio was added to the corn stover at a dose of 20% enzyme by weight with respect to the glucan in the corn stover. The augers were insulated and had 67° C. heating water recirculating around each auger in a jacket. The temperatures inside the auger were typically measured to be 45 to 50° C. with 50° C. as the target. The solid phase was moved up the auger using a screw conveyer and passed to the next auger. After the solids reached the end of the fourth auger, they were recycled back into the start of the first auger when the fresh material was added to the system. The liquid phase was separated from the solids using a mesh screen located near the beginning of the auger but after the inlet. From the auger, the liquid was run through a vibrating screen (Sweco, Florence, Ky.) with a 100 μm screen. The solids that did not pass through the screen were rejected back into the auger system. The liquid was sent to a TFF system. In the TFF system, a 0.9 m² module containing a 150 kDa polyether sulfone (PES) membrane (SmartFlow Technologies, Apex, N.C.) was utilized. The retentate was periodically recycled back into the auger system while the permeate was removed from the system.

Figure 8:
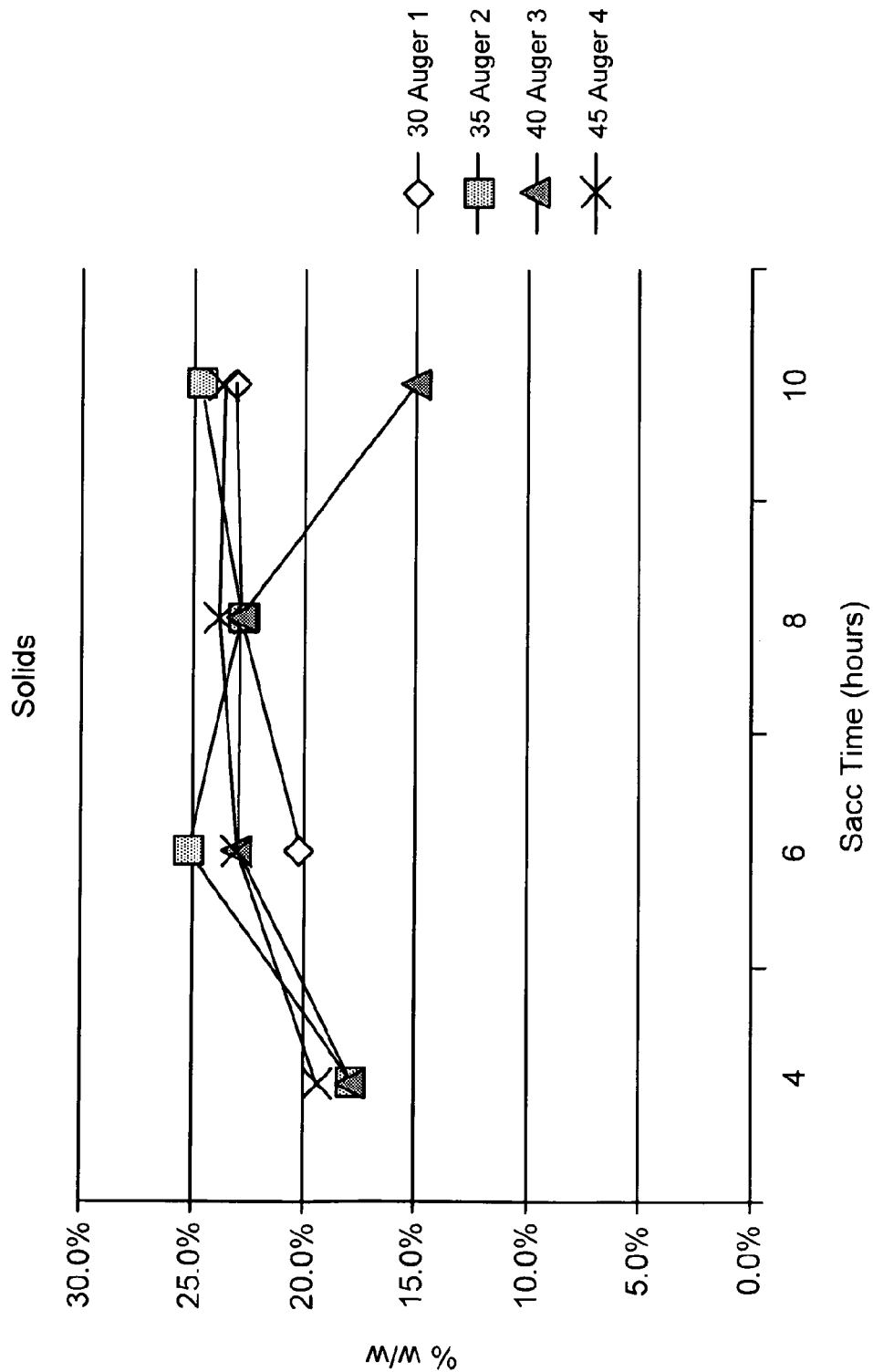
FIG. 8 shows solids concentration in each auger as a function of time as described in Example 2.

FIG. 8 displays the solids concentration in each auger as a function of time. It was found that the auger system could remove enough water through the mesh at the bottom of the auger that solids concentration between 22% and 25% were present in the auger during the saccharification. This value was much higher than the solids of 16%, which were present in the feed.

Figure 9:
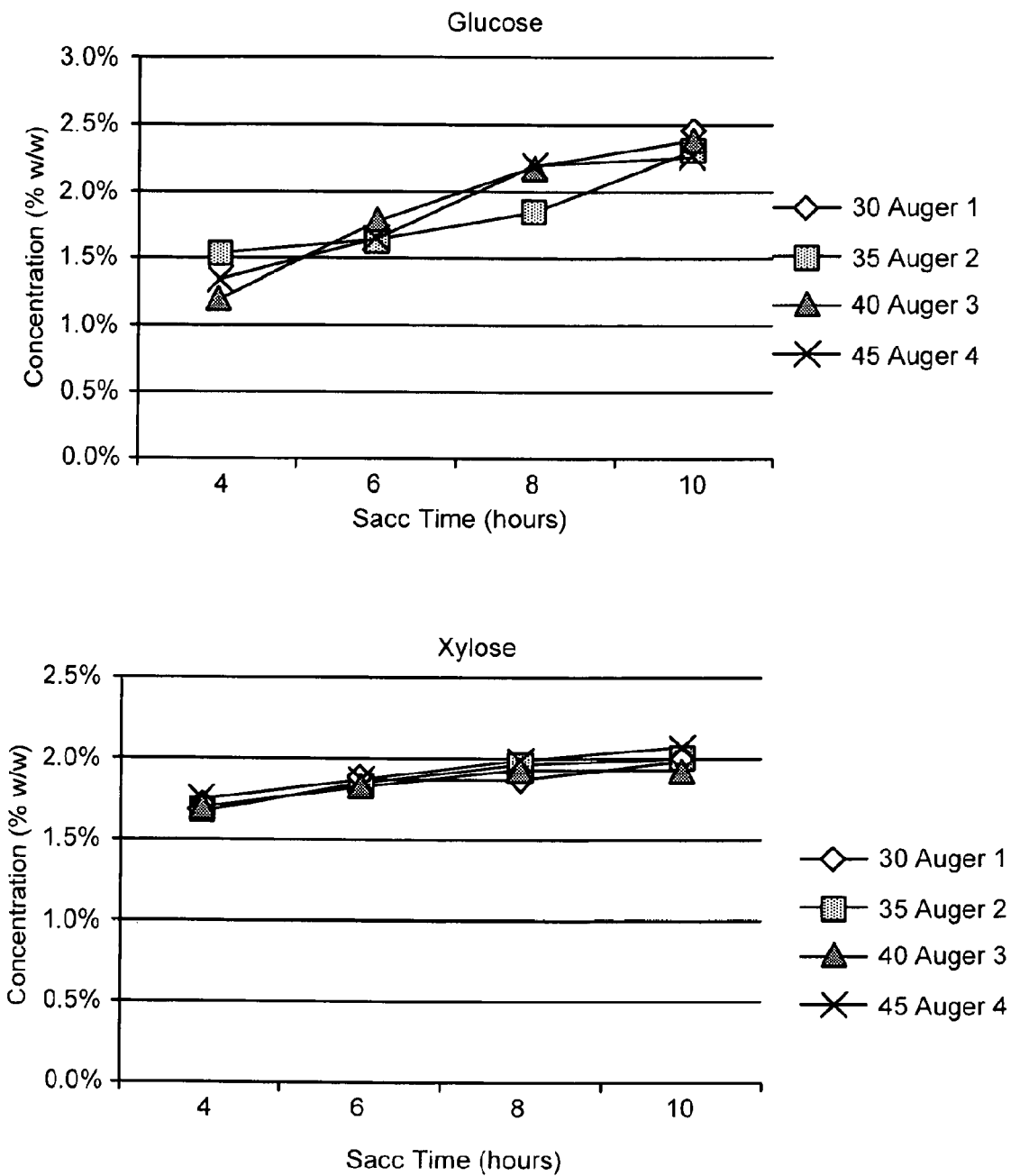
FIG. 9 shows glucose and xylose concentration in each auger as a function of time as described in Example 2.

FIG. 9 illustrates the glucose and xylose concentrations in each auger as a function of time. As FIG. 9 illustrates, the sugar concentration in all 4 augers was similar, which was likely due to the liquid and retentate recycle that was performed. The final (at t=12) glucose from glucan yield was 37%. The final xylose from xlyan yield was 81%.

Example 3

This example demonstrates a system for generating sugar from biomass where the enzymes are contacted with biomass under conditions suitable to hydrolyze the biomass into sugars using augers.

In this example, the liquid phase was separated from the solid phase using a screen and a vibrating screen. The liquid phase was stored under conditions suitable to produce sugars. The liquid was separated using a TFF membrane into a permeate containing sugar and some dissolved solids and a retentate containing enzymes, sugar, and any remaining particulate solids. The retentate was then recombined with the solids in the auger system via a counter current wash in each auger. The biomass used in this example was bagasse, and the system was operated continuously over 10 days.

Figure 10A:
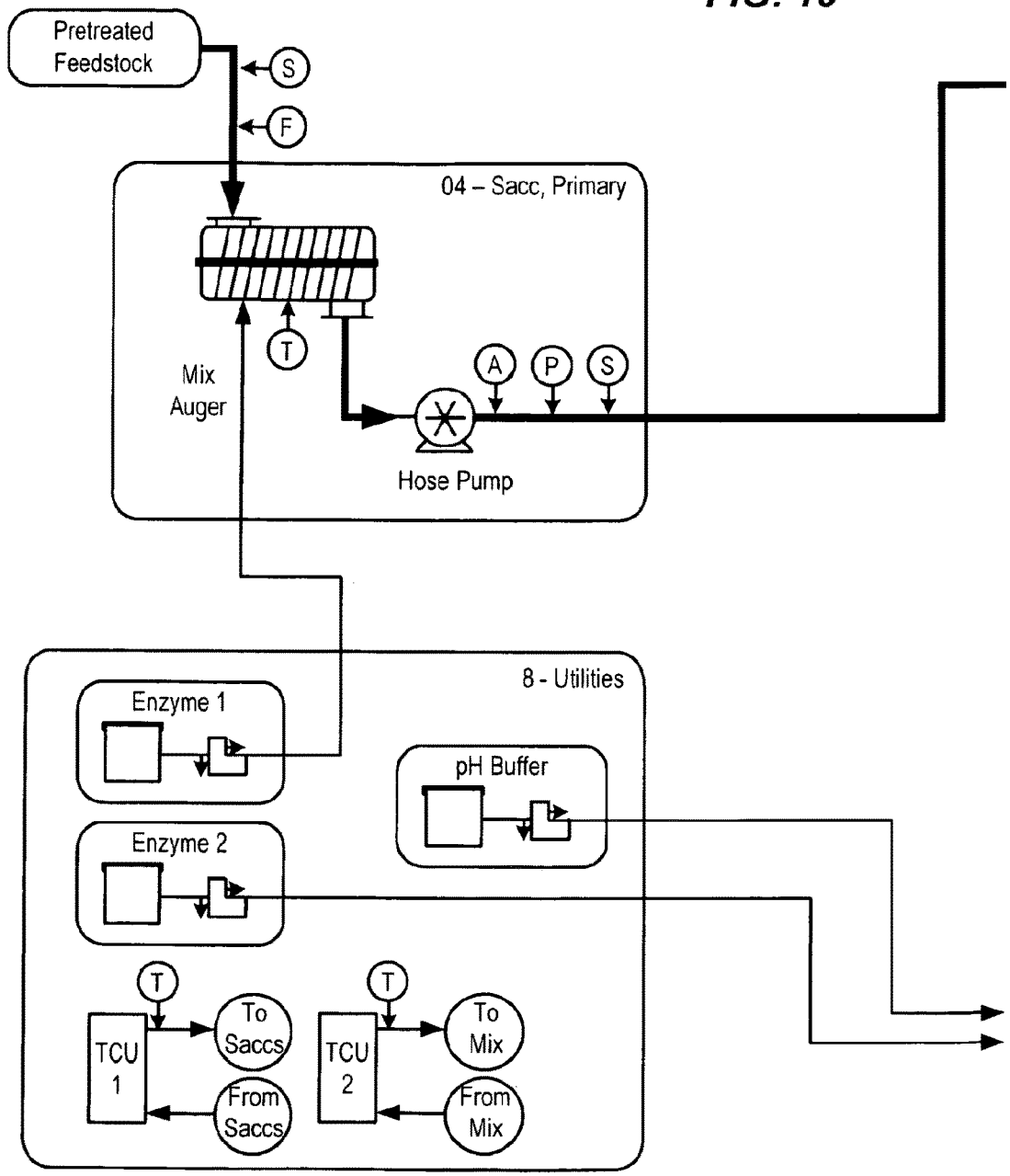
FIG. 10 illustrates the process flow diagram of the saccharification system as described in Example 3.
Figure 10B:
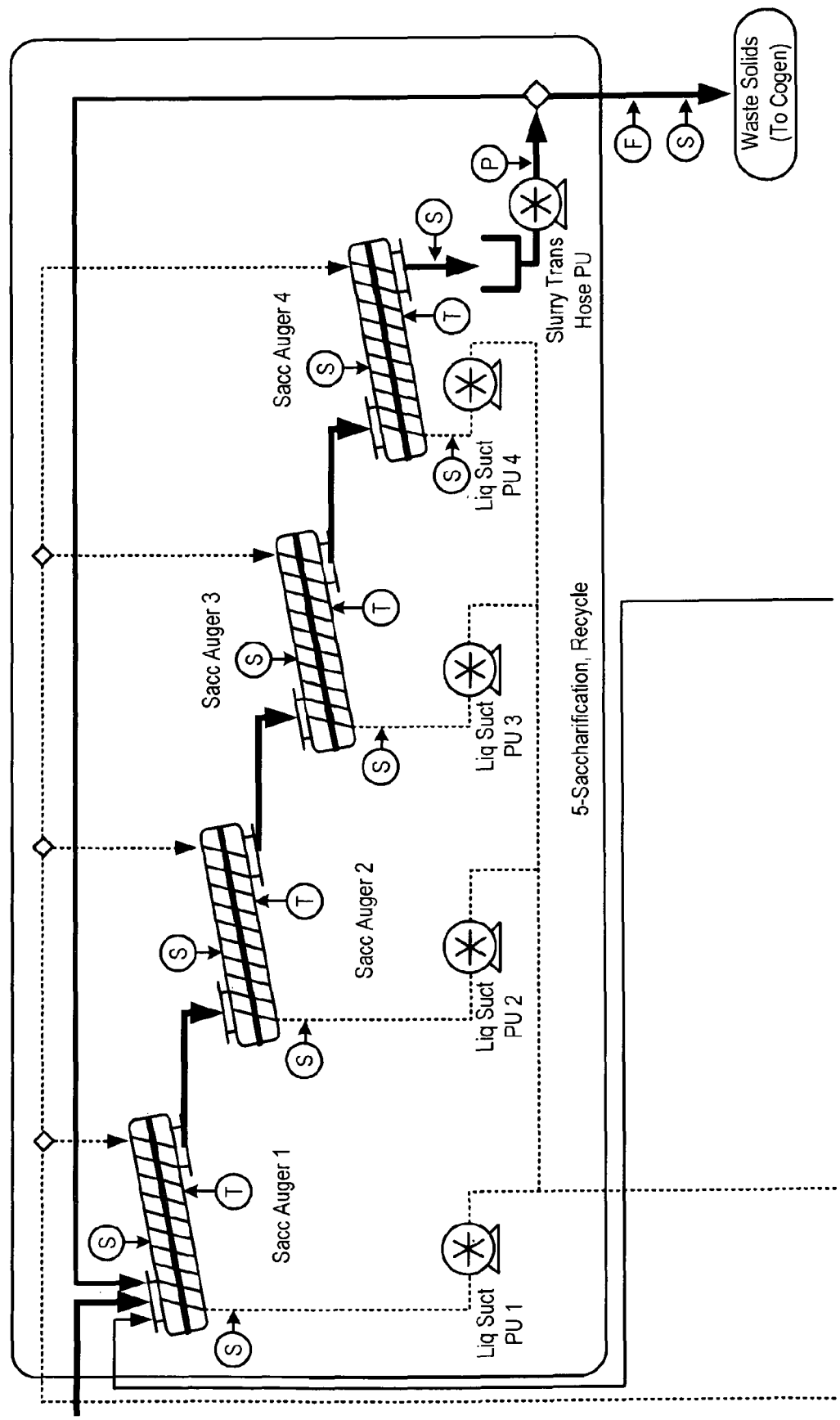
Figure 10C:
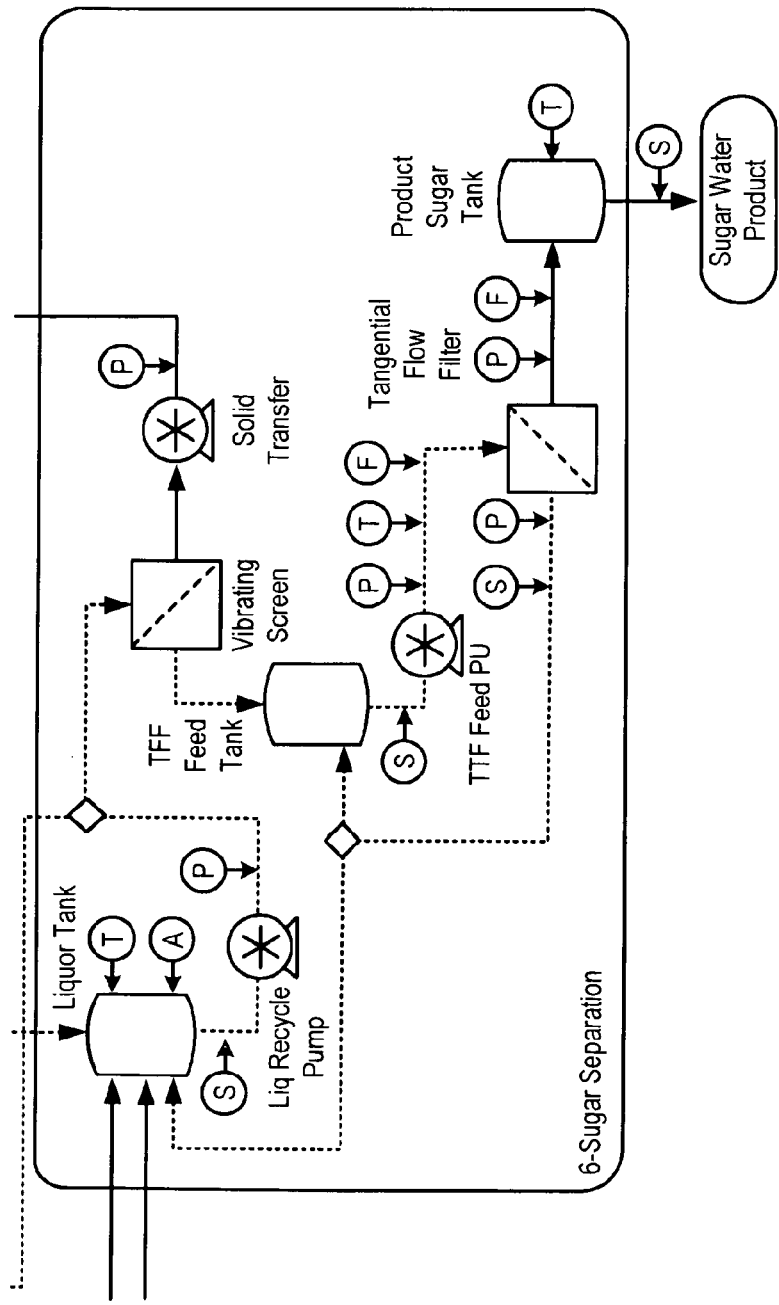

The overall schematic of the system for generating sugar from biomass is depicted in FIG. 10. The bagasse biomass was pretreated for 40 minutes at 179° C. The bagasse slurry was transferred into the first of 5 augers at 12% solids. This first auger was called the mix auger in FIG. 10 and no liquid recycle occurred into this auger. Accellerase Trio was added to the bagasse in the mix auger at a dose of 20% enzyme by weight with respect to the glucan in the bagasse. Additionally, polyethyl glycol (PEG) was added to the biomass in the mix auger at a dose of 2% PEG by mass with respect to the solids mass in the solution. The augers were insulated and had 67° C. heating water recirculating around each auger in a jacket. The temperatures inside the auger had 50° C. as the target. The solid phase was moved through the mix auger using a screw conveyer and was pumped to the next auger, which was the first of four saccharification augers (see FIG. 10). In the saccharification augers, the liquid phase was separated from the solids using a mesh screen located at or near the beginning of the auger but after the inlet. The solid phase was moved through each saccharification auger using a screw conveyer and was pumped to the next auger. After the solids reached the end of the fourth saccharification auger, they were recycled back into the start of the first saccharification auger where the material from the mix auger was also added. To aid in the liquor removal from the saccharification augers, these augers were operated with a 3° incline from start to end. From the auger, the liquid was run through a vibrating screen (Sweco, Florence, Ky.) with a 45 μm screen. The solids that did not pass through the screen were rejected back into the auger system. The liquid was sent to a TFF system. In the TFF system, a 9.8 m² module containing a 150 kDa polyether sulfone (PES) membrane (SmartFlow Technologies, Apex, N.C.) was utilized. The retentate was periodically recycled back into the saccharification augers while the permeate was removed from the system.

The overall mass and solids mass balances are shown in Table 1. The overall mass balanced closed to within 0.03%. Based upon the glucan and glucose mass balance, the overall glucose from glucan yield was 56%. Based upon the xylan and xlylose mass balance, the overall xylose from xlyan yield was 67%.

TABLE 1

The overall system mass balance. Note: Total solids includes measured volatiles.

| Location | Total | Total Solids | Water | Other Solids | Glucan | Xylan | Glucose | Xylose | Volatiles |
|---|---|---|---|---|---|---|---|---|---|
| In PT System | 16690 | 1931 | 14759 | 811 | 753 | 367 | 0 | 0 | 0 |
| Permeate | 13645 | 858 | 12787 | 203 | 0 | 0 | 367 | 219 | 68 |
| Filtrate | 1690 | 291 | 1399 | 133 | 41 | 5 | 48 | 28 | 35 |
| Final Solids | 213 | 61 | 152 | 26 | 20 | 3 | 6.8 | 3.7 | 0.9 |
| Samples/ Losses | 1148 | 288 | 861 | 211 | 53 | 6 | 10 | 5.9 | 1.5 |

Figure 11:
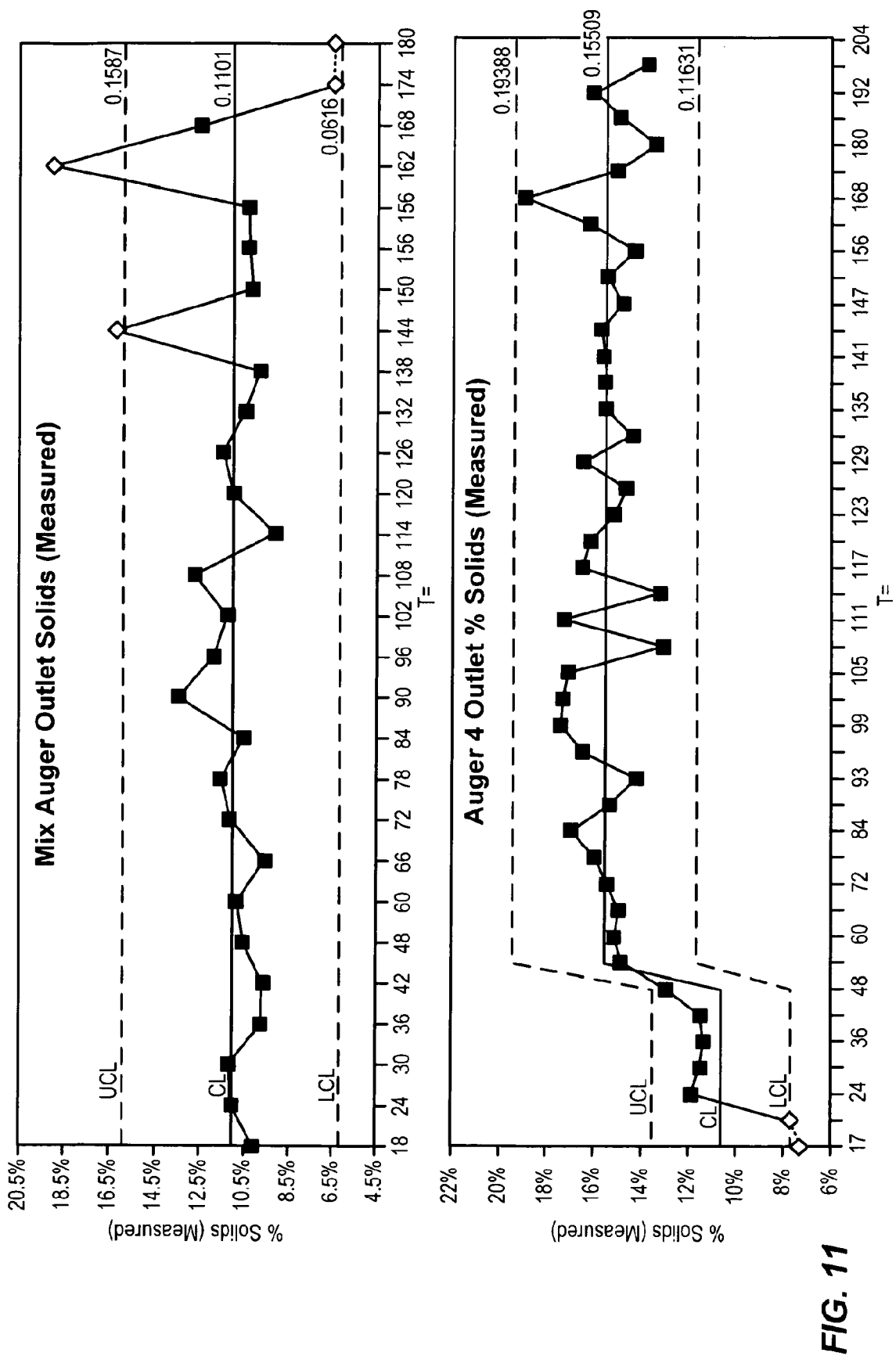
FIG. 11 shows control charts displaying the % total solids for the mix auger, auger 4, and filtrate tank as described in Example 3. Measured solids averaged 11% in the mix auger, increased to 15.5% in the saccharification augers and averaged 11.5% in the TFF feed.
Figure 11:
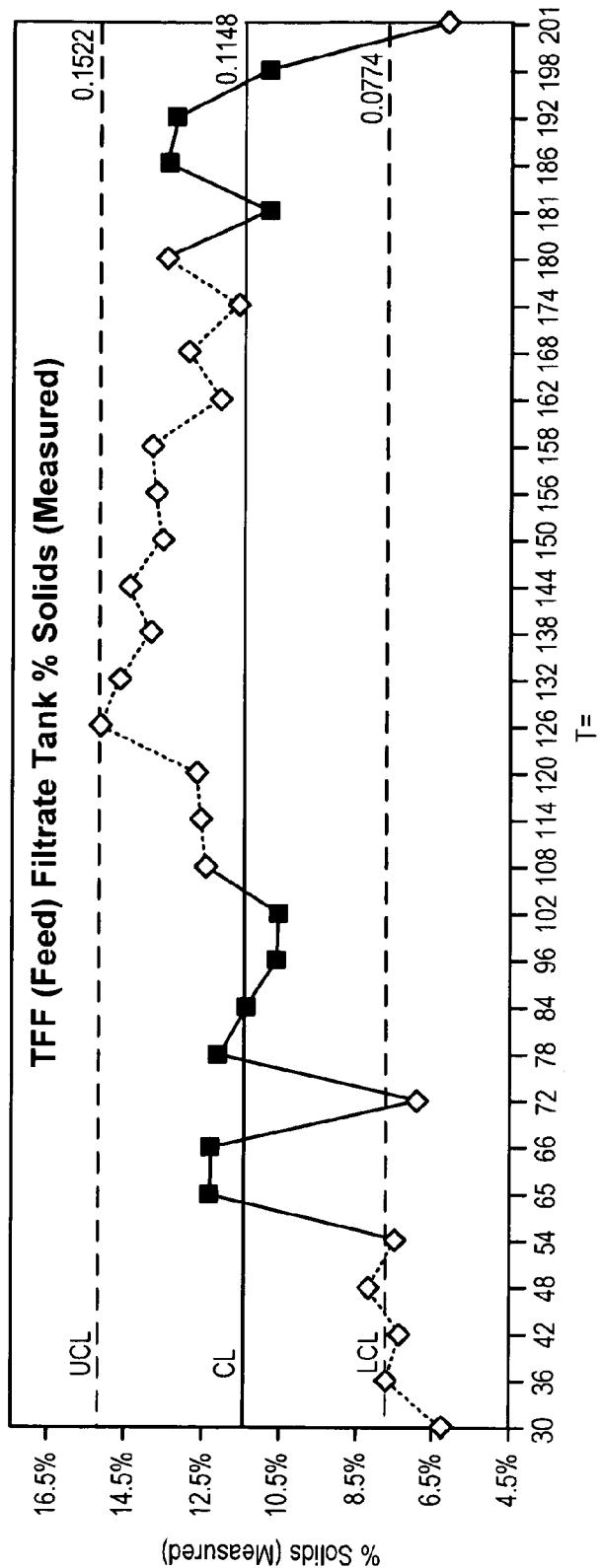
Figure 12:
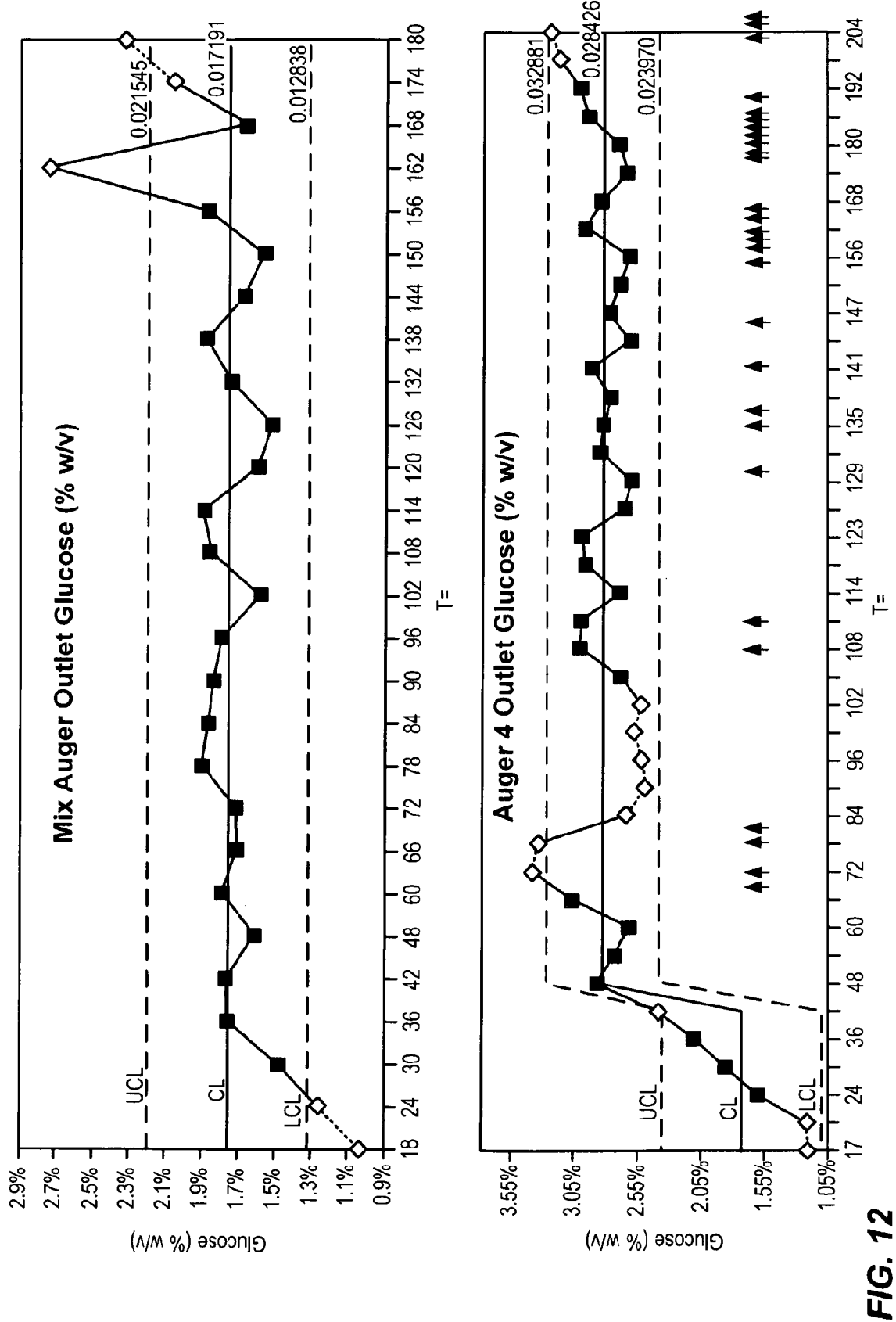
FIG. 12 shows control charts displaying the glucose concentration for the mix auger, auger 4, and filtrate tank as described in Example 3. Glucose concentration averaged 1.7% in the mix auger, increased to 2.8% in the saccharification augers and 3.0% in the TFF feed. The arrows denote when filtration was recycled back to the auger system.
Figure 12:
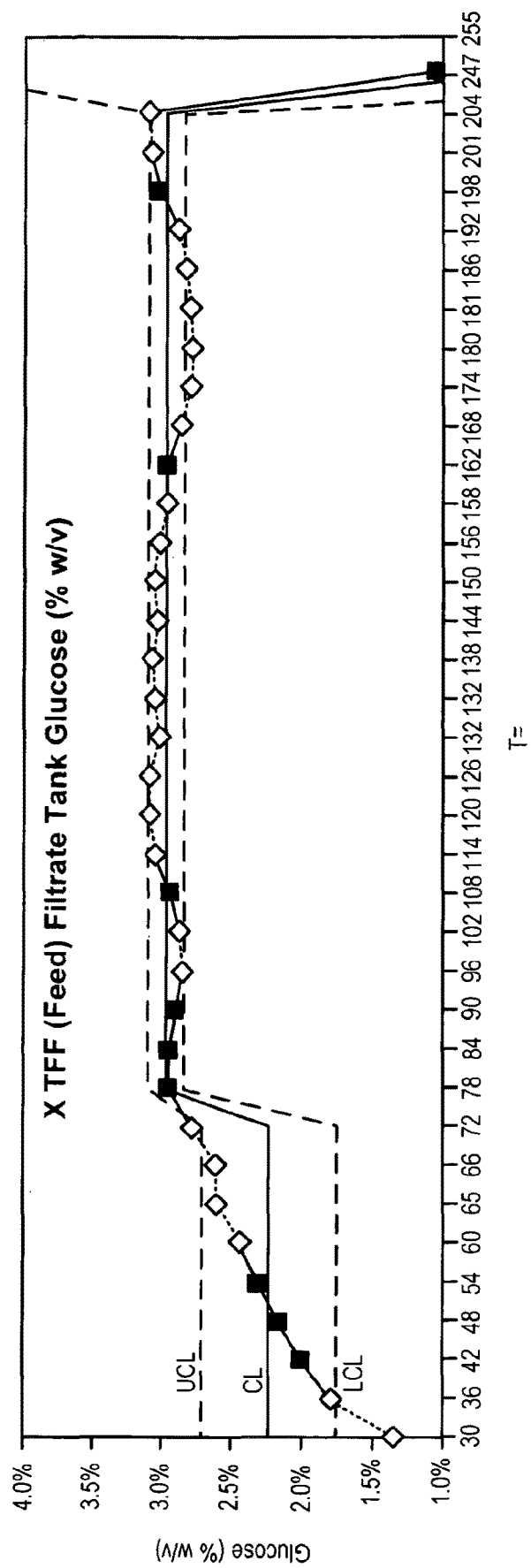
Figure 13:
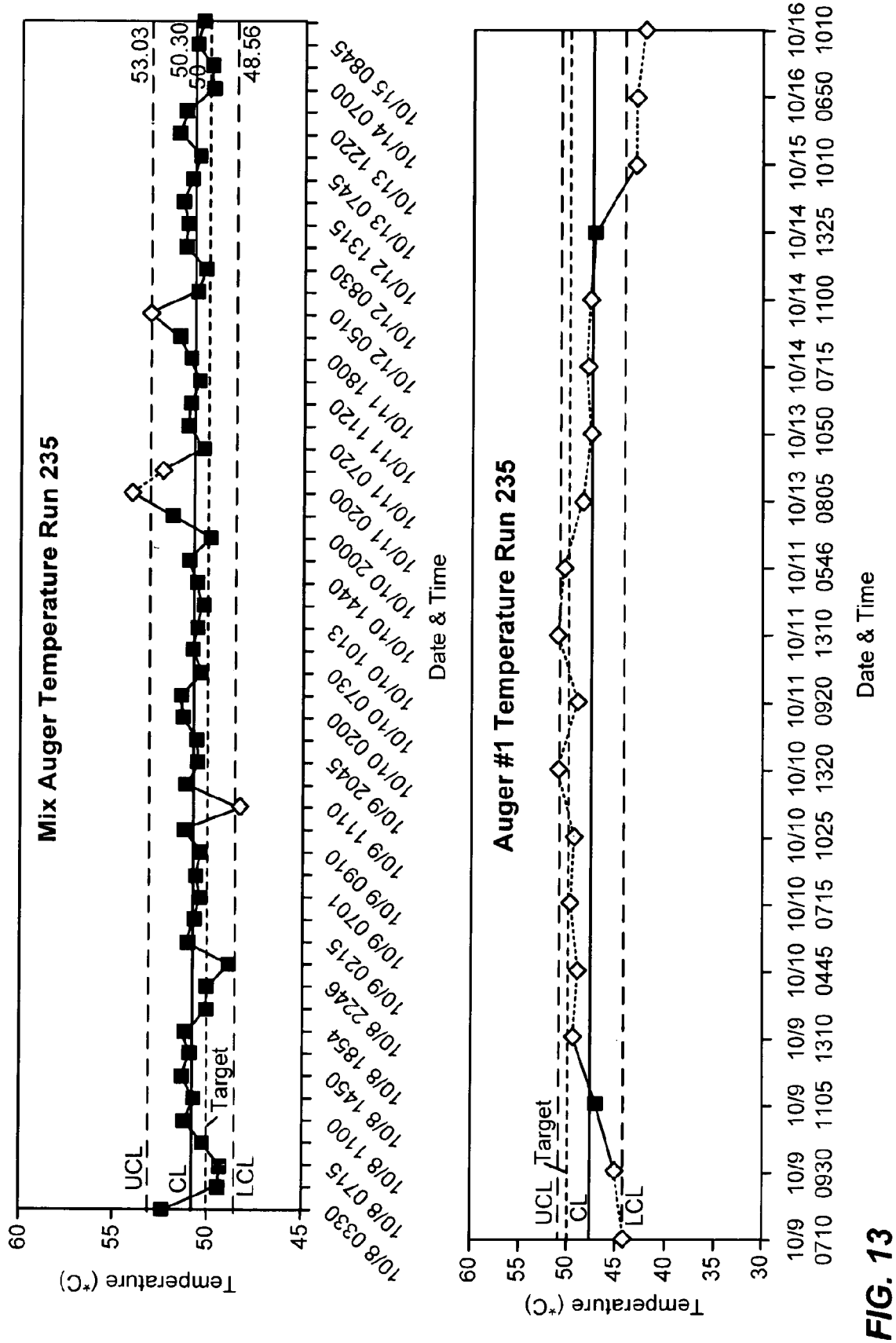
FIG. 13 shows control charts displaying the temperatures for the mix auger, auger 1, and auger 3 as described in Example 3.
Figure 13:
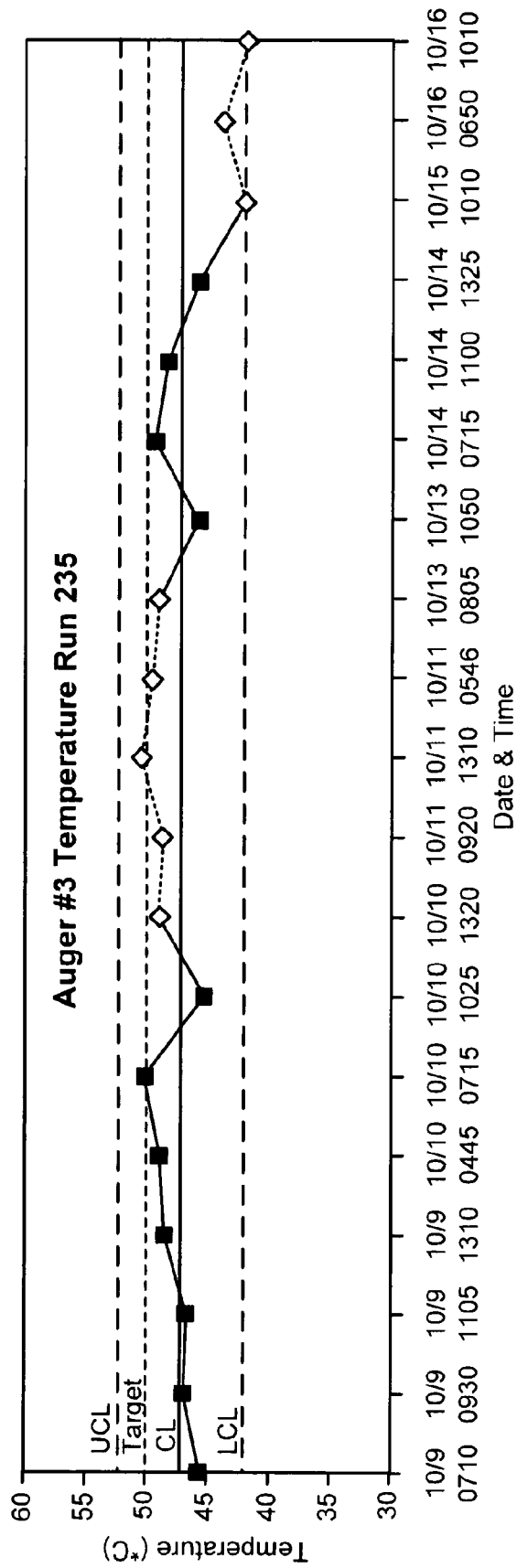

FIGS. 11, 12, and 13 display the control charts for solids, glucose, and temperature in different parts of the system. FIG. 11 illustrates that the average measured solids were 11.0% in the mix auger, 15.5% in saccharification auger 4, and 11.5% in the TFF filtrate tank. Additionally, the measured solids in the system were mostly well controlled in the mix auger and the saccharification auger 4. The solids concentration in the saccharification augers was higher than in the mix auger due to the removal of the liquid phase in the saccharification augers. In the filtrate tank the solids tended to be above the average for long periods of time and thus show up as out of control. This long period of being out of control was likely due to the concentration of solids in the TFF feed tank as the TFF system was operating.

FIG. 12 displays that the glucose concentration was mostly well controlled during the run. In contrast, auger 4 had an out of control point at around 78 hours where the concentration dropped from 3.3% to 2.5%. This period corresponds to the time just after the completion of the recycle of filtrate material back into the auger 4. The concentration remained low until the next recycle of filtrate began. The glucose concentration increase after the filtrate recycle supports the hypothesis that enzyme recycle will help drive an increase in yield. For the remainder of the run, the saccharification auger 4 glucose concentration remained in control until the system approached the end of the run. Dramatic changes in the sugar concentrate were not seen again in association with the filtrate recycle as was observed after the first few recycles. In contrast to both the mix auger and auger 4, the TFF filtrate tank had a much narrower band and tended to trend above or below the average and thus was out of control for much of the process. These shifts are again likely due to TFF operation and should try to be further understood so that higher glucose concentrations in the TFF filtrate tank can be achieved. Based upon the measured 11.7% solids loading and 39% glucan composition, the mix auger had an average conversion of 34% (1.72/5.07), the saccharification augers had an average conversion of 22%, and the TFF filtrate tank had an average conversion of 3%. Therefore, by maintaining the liquid phase in the TFF filtrate tank at appropriate conditions for saccharification the overall process yield was improved. The sum of the conversion in each individual component adds up to a total glucan to glucose conversion of 59%, which is close to the calculated conversion of 56% based upon the glucan mass balance.

FIG. 13 displays the temperature in the mix auger, saccharification auger 1, and saccharification auger 3. In the mix auger and saccharification auger 1, the temperature was mostly under control with an average temperature of 50.8° C. in the mix auger. In auger 1, the average temperature was 47.8° C., but during the middle of the run the temperatures are consistently above average and are very close to the target temperature of 50° C. Saccharification auger 3 had a lower average temperature than saccharification auger 1 with an average of 47.2° C.

Figure 14:
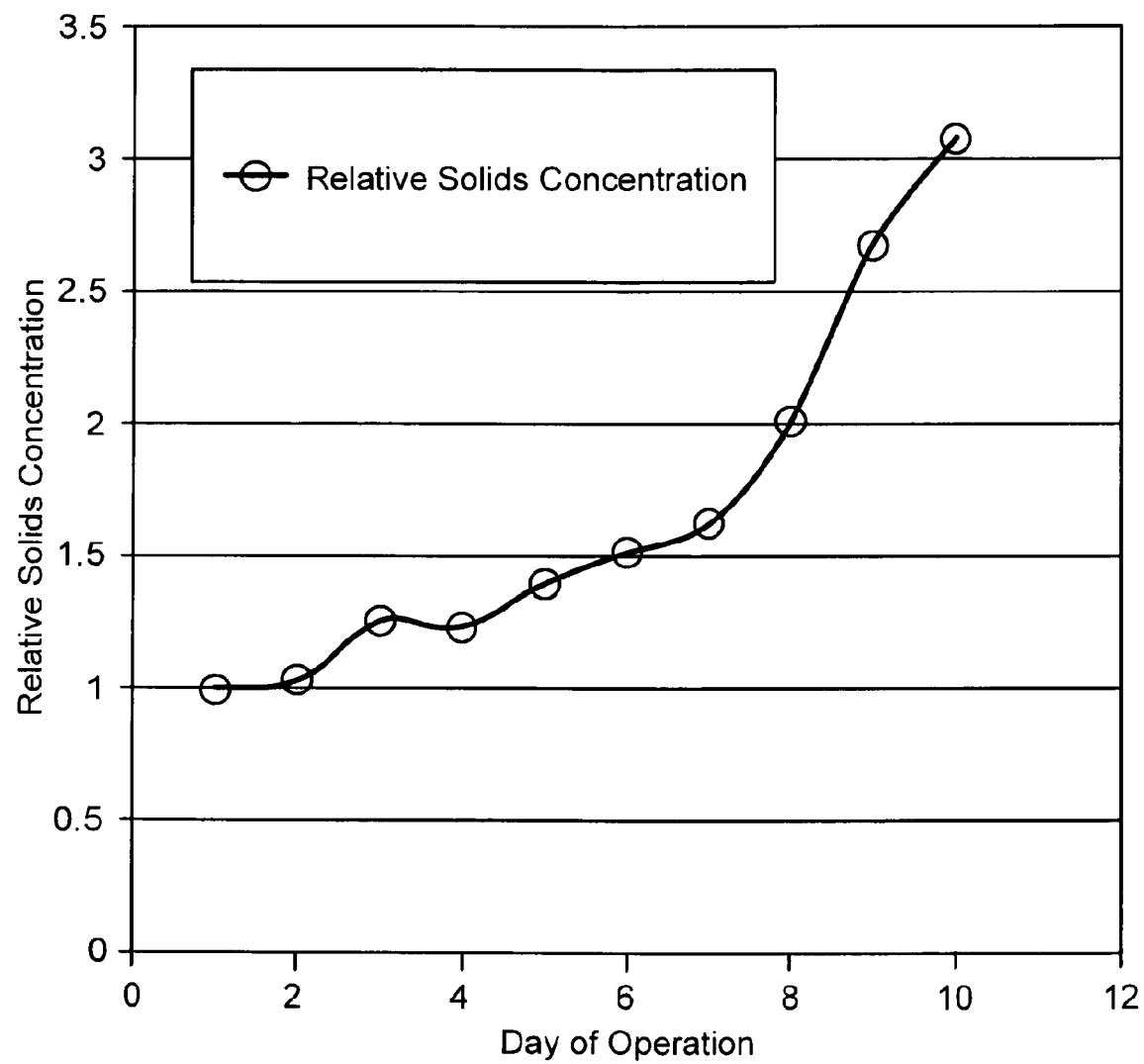
FIG. 14 shows the calculated increased in solids concentration in the saccharification system due to removal of the liquid phase out the permeate, as described in Example 3.

Because solids were being accumulated in the system due to the removal of the sugar and water stream out of the permeate, the expected solids concentration in the saccharification augers would be 1.2× to 2.0× the initial loading into the system during the first 8 days and increase to 3× once the feed into the auger stopped (FIG. 14).

Figure 15A:
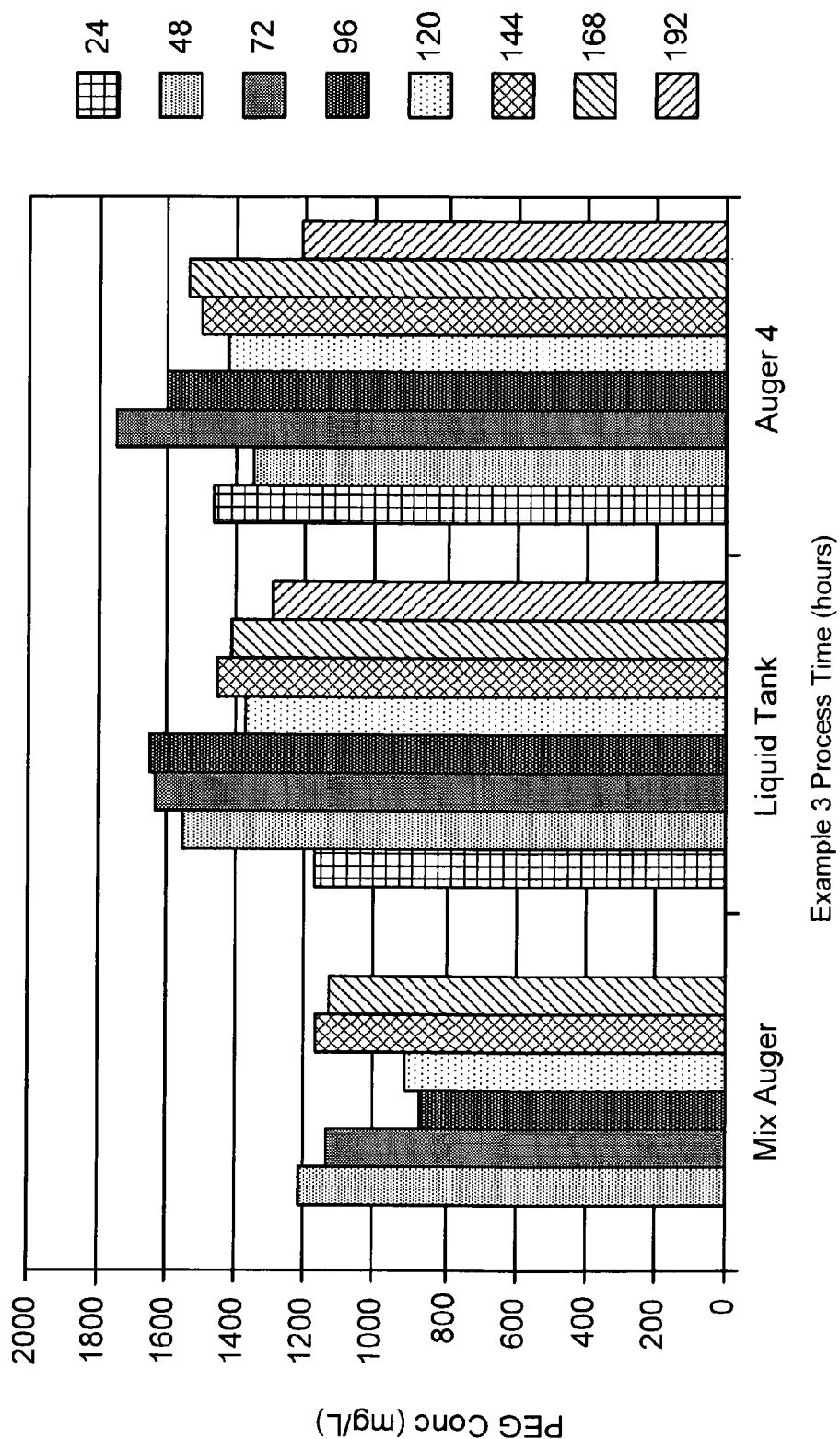
FIG. 15A shows the PEG concentration in the mix auger, liquor tank, and saccharification auger 4 at different points in the process described in Example 3.
Figure 15B:
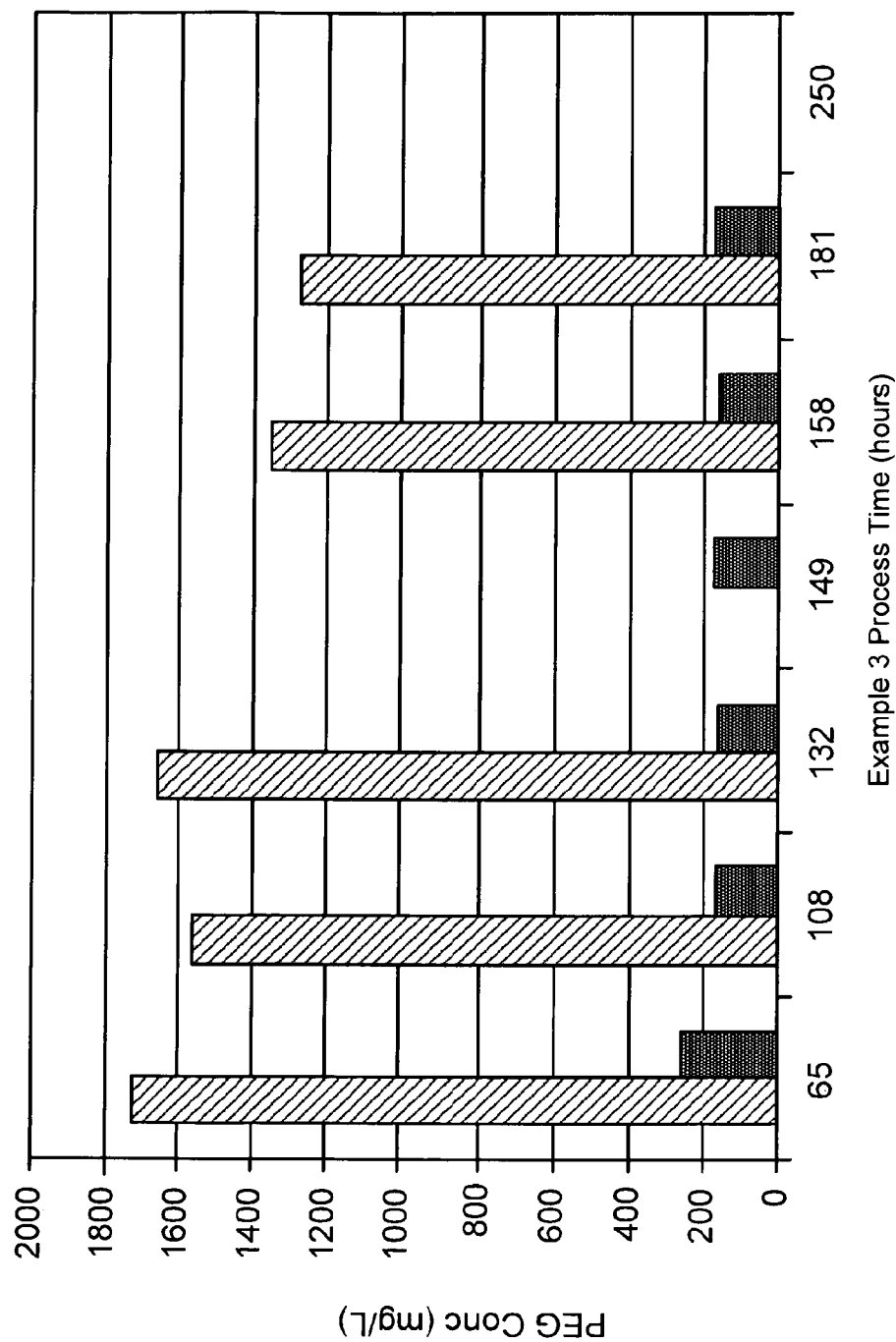
FIG. 15B shows the PEG concentration in the filtrate (TFF Concentrate) and permeate tanks at different times in the run described in Example 3.

This example further demonstrates that the PEG and enzyme could be concentrated in the TFF and recycled back to the auger system. FIG. 15A illustrates the measured PEG concentrations in the mix auger (without any recycle) and the saccharification augers which did have recycle. The measured PEG concentration in the saccharification augers averaged 1.4 times the concentration in the mixing auger. This value was in the same range as the 1.2× to 2.0× increase in solids concentration that was predicted looking at the process flow rates which may indicate that the PEG was concentrated in a similar manner as the solids. The concentration of PEG in the filtrate (or TFF concentrate) and permeate tanks at the end of selected TFF cycles is shown in FIG. 15B. The concentration of PEG in the filtrate tank (or TFF concentrate tank) was typically 9× the concentration in the permeate. Summing up the PEG concentration from each permeate batch indicated that only 2.5 kg of the 39.2 kg of PEG added to the system was lost in the permeate. This equates to losses of only 6.3% of the initial PEG out of the permeate, which was much less than the over 80% of total mass that exited the system through the TFF membrane.

Figure 16:
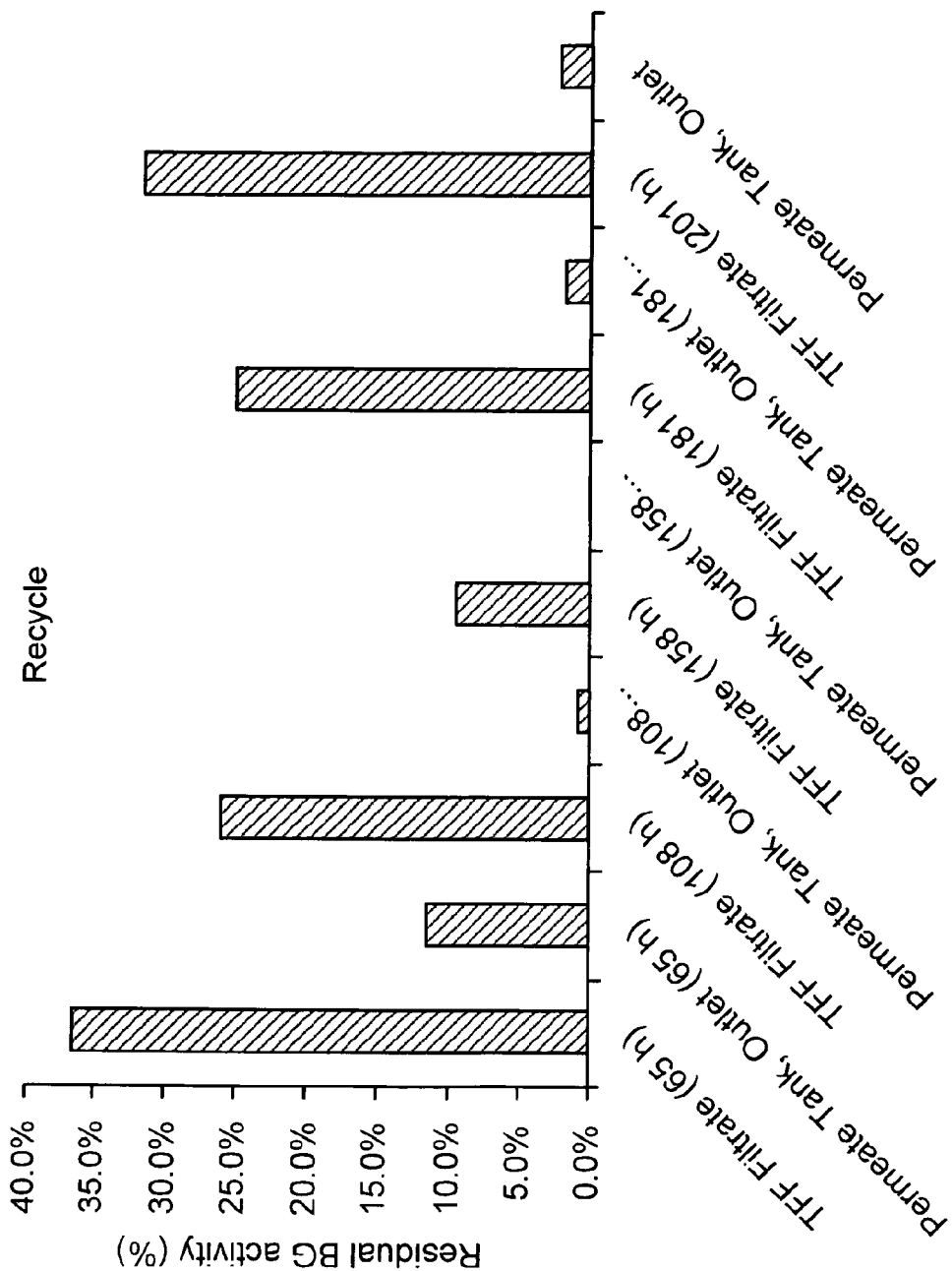
FIG. 16 shows the beta-glucosidase (BG) enzyme activity in the TFF filtrate tank (concentrate) and permeate tank as described in Example 3.

FIG. 16 illustrates the beta-glucosidase (BG) concentration in the TFF permeate and TFF concentrate during various TFF cycles. In all cases, the TFF concentrate had much higher BG activity than the permeate contained. Averaging the 5 cycles upon which enzyme activity assays were performed, an average of 4% of the original BG activity passed through the filter. The TFF filtrate had 26% of the original enzyme activity. The contents of this tank were then recycled back to the saccharification augers to increase the overall enzyme concentration in the system. These data confirm that the TFF recycle was retaining BG in addition to the PEG and that the opportunity exists to "reuse" or "recycle" the enzymes.

TFF operations consisted of 9 filtration cycles that generated a total of 3504.5 gallons permeate liquor. This value represents 82% of the liquid that was fed into the system. Key figures for each filtration cycle are shown in Table 2.

The net flux, which was calculated from the total amount of permeate generated over the filtration period, varied between cycles. This variation was the result of differences in filtrate solids (average solids and pellet weight) and operating pressures.

TABLE 2

Selected TFF performance parameters

| Cycle | CSP Start Time | Duration (hours) | Perm Gen (gal) | Net Flux (LMH) |
|---|---|---|---|---|
| 1 | 60:53:00 | 3:07 | 714.4 | 88.42 |
| 2 | 102:40:00 | 6:10 | 672.2 | 42.05 |
| 3 | 123:38:00 | 8:45 | 343.5 | 15.14 |
| 4 | 137:45:00 | 5:09 | 173.9 | 13.03 |
| 5 | 154:35:00 | 5:52 | 384.1 | 25.25 |
| 6 | 164:09:00 | 4:04 | 155.3 | 14.73 |
| 7 | 172:22:00 | 8:57 | 316.1 | 13.62 |
| 8 | 187:54:00 | 14:29 | 594.6 | 15.84 |
| 9 | 247:08:00 | 3:35 | 156.2 | 16.82 |

Example 4

This example demonstrates the concentration of tangential flow filtration (TFF) permeate using a reverse osmosis (RO) system.

Approximately 750 gallon of TFF permeate with the composition show in the first column of Table 3 was concentrated using a RO system using a spiral wound element of type 8040-ACM@-TSFA (Synder Filtration, Vacaville, Calif.). The system was operated for just over 6 hours. Concentrations of sugar and other hydrolysis products were determined using HPLC analysis.

The results indicate that it is feasible to concentrate the TFF permeate in the RO system. Table 3 indicates that the total sugar concentration was increased 1.8× from 4.1% w/v to 7.4% w/v.

TABLE 3

Components concentration during Reverse Osmosis (RO) membrane concentration of TFF permeate at each hour of the RO system run.

| Time | 0 | 1 | 2 | 3 | 4 | 5 | 6 | 6.75 | T = Final | Effluent Tank |
|---|---|---|---|---|---|---|---|---|---|---|
| Glucose | 2.43 | 2.76 | 3.13 | 3.47 | 3.76 | 4.00 | 4.23 | 4.38 | 4.38 | 0.07 |
| Xylose | 1.60 | 1.82 | 2.06 | 2.29 | 2.48 | 2.64 | 2.79 | 2.89 | 2.89 | 0.05 |
| Arabinose | 0.08 | 0.09 | 0.10 | 0.11 | 0.09 | 0.12 | 0.13 | 0.14 | 0.14 | 0.00 |
| Total Sugar | 4.11 | 4.67 | 5.29 | 5.87 | 6.33 | 6.76 | 7.15 | 7.40 | 7.41 | 0.12 |
| Acetic Acid | 0.28 | 0.32 | 0.35 | 0.38 | 0.41 | 0.43 | 0.45 | 0.46 | 0.46 | 0.02 |
| Ethanol | 0.14 | 0.15 | 0.17 | 0.18 | 0.18 | 0.19 | 0.19 | 0.19 | 0.18 | 0.02 |
| 5-H MF | 64.1 | 72.6 | 81.4 | 89.8 | 96.5 | 102.4 | 107.3 | 110.9 | 110.6 | 2.8 |
| Furfural | 402.7 | 436.9 | 472.3 | 501.2 | 521.4 | 539.1 | 551.5 | 562.4 | 561.2 | 32.8 |

Glucose, xylose, arabinose, total sugar, acetic acid and ethanol values are % w/v. 5-HMF and Furfural are in PPM.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes. In the claims appended hereto, the term "a" or "an" is intended to mean "one or more." The term "comprise" and variations thereof such as "comprises" and "comprising," when preceding the recitation of a step or an element, are intended to mean that the addition of further steps or elements is optional and not excluded.

What is claimed is:

1. A method for generating glucose from biomass, comprising:
   (a) pretreating the biomass at a temperature of about 150° C. to about 210° C. and a pH of 4.0 to 6.0;
   (b) contacting the biomass with cellulase and hemicellulase under conditions suitable to hydrolyze components of the biomass to sugars, thereby producing a mixture of solids, liquids, and sugars;
   (c) once formed, separating the mixture into a liquid phase containing sugars and a solids phase;
   (d) prior to further hydrolysis steps, washing the solids phase to remove at least a portion of the sugars, thereby forming a washed solids phase, wherein the sugars inhibit saccharification enzyme activity; followed by
   (e) incubating the washed solids phase with cellulase and hemicellulase to hydrolyze components of the solid phase to glucose, thereby producing additional glucose; then
   (f) separating the liquid phase into a permeate comprising dissolved solids and sugars and a retentate comprising undissolved solids, enzymes, and sugars; and
   (g) combining the retentate with the biomass or solids phase under conditions wherein the biomass is converted to glucose.

2. The method of claim 1, wherein the retentate is combined with additional unhydrolyzed biomass under conditions suitable to hydrolyze components of the biomass to sugars.

3. The method of claim 1, further comprising washing the retentate to remove at least a portion of the sugars, thereby forming a washed retentate.

4. The method of claim 3, wherein the washed retentate is further separated into a liquid comprising sugars and solids comprising enzymes, and optionally wherein the sugars are further concentrated by reverse osmosis.

5. The method of claim 1, wherein the liquid phase is separated from the solids phase by a screen, vibrating screen, a press, or a centrifuge.

6. The method of claim 1, wherein the liquid phase is incubated under conditions suitable to produce sugars.

7. The method of claim 1, wherein the permeate is separated from the retentate by a filter or membrane, and optionally separating the permeate into a concentrated sugars portion and a liquid portion by reverse osmosis.

8. The method of claim 1, further comprising separating the washed solids phase into a liquid comprising sugars, and solids.

9. The method of claim 1, wherein the contacting occurs in an auger.

10. The method of claim 9, wherein step (e) comprises a counter-current flow such that the liquid phase moves in an opposite direction to the solid phase.

11. The method of claim 1, further comprising concentrating the solids phase and separating at least a portion of any remaining liquid from the solids.

12. The method of claim 1, wherein step (e) comprises a counter-current flow such that the liquids move in an opposite direction to the solids.

13. The method of claim 9,
wherein the contacting occurs in a first auger, the first auger comprising:
   a solids inlet;
   a screw inside the auger to direct a solid mass in the auger from a first end to a second end;
   a liquid outlet at the first end;
   a solids outlet at the second end; and
   a separator suitable for separating the biomass into a liquid phase and a solids phase and positioned between (i) the liquid outlet and (ii) the screw and the solids outlet; and
the method further comprises contacting a solids phase from the first auger with at least a second auger comprising:
   an inlet in fluid communication with the solids outlet for receiving a solids mass from the first auger; and
   a solids outlet.

14. The method of claim 1, wherein the biomass comprises corn stover.

15. The method of claim 1, wherein the pretreatment duration is 5 to 60 minutes.

16. The method of claim 1, wherein the yield of glucose from the biomass is increased without having to increase the solids concentration of the biomass above 30% w/v.

* * * * *